United States Patent [19]

Jikihara et al.

[11] Patent Number: 4,971,620
[45] Date of Patent: Nov. 20, 1990

[54] SULFONAMIDE AND HERBICIDE CONTAINING THE SAME AS ACTIVE INGREDIENT

[75] Inventors: Tetsuo Jikihara, Tokyo; Manabu Katsurada, Yokohama; Toyohiko Shike; Osamu Ikeda, both of Machida; Hisao Watanabe, Yokohama; Tetsuo Takematsu; Koichi Yoneyama, both of Utsunomiya, all of Japan

[73] Assignee: Mitsubishi Kasei Corporation, Tokyo, Japan

[21] Appl. No.: 302,253

[22] Filed: Jan. 27, 1989

[30] Foreign Application Priority Data

Jan. 28, 1988 [JP] Japan .................... 63-18458

[51] Int. Cl.$^5$ .................... A01N 41/06; C07C 143/80; C07C 143/68
[52] U.S. Cl. ........................... 71/103; 71/88; 71/105; 549/355; 549/404; 549/408; 549/462; 558/48; 558/413; 564/85; 564/87; 564/89; 564/92
[58] Field of Search ........... 564/92, 89, 87, 85, 564/84; 558/48, 413, 422; 71/103, 105, 88; 549/404, 408, 462, 355

[56] References Cited

U.S. PATENT DOCUMENTS 4,157,257 6/1979 Takematsu et al. .............. 71/103
4,233,061 11/1980 Takematsu et al. .............. 71/103

FOREIGN PATENT DOCUMENTS 81425 6/1983 European Pat. Off. .

OTHER PUBLICATIONS

J. C. S. Perkin I, "Persulphate Oxidations, Part 12, Generation and Reactions of N–Methoxy–benzamidyls and –benzsulphonamidyls", by Forrester et al., p. 1112 (1979).
Journal Of The Chemical Society 1981, pp. 2435, 2442.

Primary Examiner—Nicky Chan
Attorney, Agent, or Firm—Oblon, Spivak, McClelland, Maier & Neustadt

[57] ABSTRACT

Disclosed herein is a sulfonamide compound represented by the formula (I):

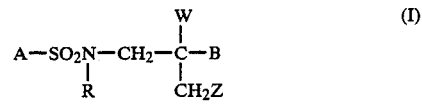

wherein A represents a phenyl group which may be substituted, B represents a phenyl group which may be substituted, R represents a lower alkyl group, a lower alkoxy group or a lower haloalkyl group, W represents a hydroxyl group or a halogen atom, and z represents a halogen atom, a lower alkylsulfonyloxy group which may be substituted, or a phenylsulfonyloxy group which may be substituted, and a herbicidal composition containing the sulfonamide compound as an effective ingredient.

6 Claims, No Drawings

SULFONAMIDE AND HERBICIDE CONTAINING THE SAME AS ACTIVE INGREDIENT

BACKGROUND OF THE INVENTION

The present invention relates to novel sulfonamides and herbicides containing the same as an effective ingredient.

Many sulfonamide compounds have conventionally been proposed as a herbicide. For example, Japanese Patent Publication No. 56-8027 (1981) discloses N-methyl-N-α, α-dimethylbenzylbenzenesulfonamide. The present inventors have proposed N-(2,3-epoxypropylene)-N-aralkylsulfonamides such as N-(2,3-epoxypropylene)-N-α-methylbenzylbenzene sulfonamide [Japanese Patent Application Laid-Open (KOKAI) No. 58-131977 (1983)] and N-[2-(pyridyl)propyl]-N-substituted sulfonamide (Japanese Patent Application Laid-Open (KOKAI) Nos. 63-215669 (1988) and 63-222158 (1988)) as a selective herbicide. Japanese Patent Application Laid-Open (KOKAI) Nos. 57-32267 (1982) and 61-286366 (1986) disclose sulfonamides having a pyridyl group as a compound having a herbicidal activity or a fungicidal activity.

An object of the present invention is to provide a herbicide which has a higher herbicidal activity than conventional sulfonamide compounds and a continuous herbicidal activity on weeds such as Echinochloa crus-galli over a long period extending from preemergence to an advanced stage of growing.

As a result of the studies undertaken by the present inventors, it has been found that a sulfonamide represented by the following formula (I):

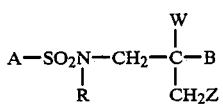

wherein A represents a phenyl group which may be substituted, B represents a phenyl group which may be substituted, R represents a lower alkyl group, a lower alkoxy group or a lower haloalkyl group, W represents a hydroxyl group or a halogen atom, and Z represents a halogen atom, a lower alkylsulfonyloxy group which may be substituted, or a phenylsulfonyloxy group which may be substituted, has a very strong herbicidal effect on Echinochloa crus-galli from preemergence to an advanced stage of growing and cause little damage to paddy-rice plants. On the basis of this finding, the present invention has been achieved.

SUMMARY OF THE INVENTION

In a first aspect of the present invention, there is provided a sulfonamide compound represented by the following formula (I):

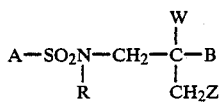

wherein A represents a phenyl group which may be substituted, B represents a phenyl group which may be substituted, R represents a lower alkyl group, a lower alkoxy group or a lower haloalkyl group, W represents a hydroxyl group or a halogen atom, and Z represents a halogen atom, a lower alkylsulfonyloxy group which may be substituted, or a phenylsulfonyloxy group which may be substituted.

In a second aspect of the present invention, there is provided a herbicidal composition which comprises a herbicidally effective amount of the sulfonamide compound represented by the above formula (I) and herbicidally acceptable carrier(s) or surfactant.

In a third aspect of the present invention, there is provided a method for killing weed which comprises applying a herbicidally effective amount of the sulfonamide compound represented by the formula (I) on the soil of flooded field or farmland.

In a fourth aspect of the present invention, there is provided a process for producing the sulfonamide compound represented by the formula (I).

DETAILED DESCRIPTION OF THE INVENTION

The present invention will be explained in detail hereinunder.

The sulfonamide used in the present invention as a herbicide is represented by the following formula (I).

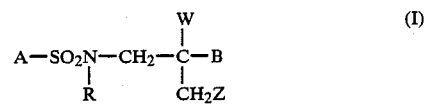

In the formula (I), A represents a phenyl group which may be substituted, and preferably represents a group represented by the formula:

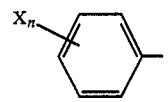

wherein X independently represents a halogen atom, a lower alkyl group, a lower haloalkyl group, a lower alkoxy group, a lower alkylsulfonyl group, a nitro group or a cyano group, and n represents 0 or an integer of 1 to 3, two adjacent Xs being able to represent in combination a group represented by the formula:

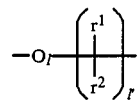

wherein $r^1$ and $r^2$ respectively represent a hydrogen atom or a lower alkyl groups, preferably a hydrogen atom or a methyl group, more preferably a hydrogen atom; l represents 0 or 1; l' represents an integer of 2 to 4 and the sum of l and l' is 3 or 4. More preferably, X represents a fluorine atom, a chlorine atom, a bromine atom, a lower alkyl group having 1 to 6 carbon atoms, a lower haloalkyl group having 1 to 2 carbon atoms, a lower alkoxy group having 1 to 6 carbon atoms, a lower alkylsulfonyl group having 1 to 2 carbon atoms, a nitro group or a cyano group, and n represents 0 or an integer of 1 to 3; or two adjacent Xs represent in combination a group represented by the formula:

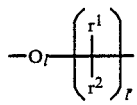

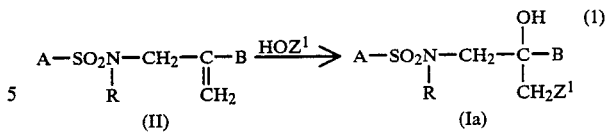

wherein l,l', r¹ and r² are the same as defined above. Particularly preferably, X represents a fluorine atom, a chlorine atom, a lower alkyl group having 1 to 4 carbon atoms, a lower alkoxy group having 1 to 4 carbon atoms, a trifluoromethyl group or a cyano group, and n represents 0 or an integer of 1 or 2; or two adjacent Xs represent in combination a group represented by —O-$_l$(CH$_2$)$_{l'}$, wherein l and l' are the same as defined above.

In the formula (I), B represents a phenyl group which may be substituted, and preferably represents a group represented by the formula:

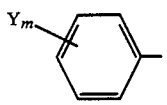

wherein Y independently represents a halogen atom, a lower alkyl group, a lower haloalkyl group, or a lower alkoxy group; more preferably a fluorine atom, a chlorine atom, a bromine atom, a lower alkyl group having 1 to 3 carbon atoms, a lower haloalkyl group having 1 to 2 carbon atoms, or a lower alkoxy group having 1 to 3 carbon atoms; particularly preferably a fluorine atom, a chlorine atom, a methyl group, a trifluoromethyl group or a methoxy group; and m represents 0, 1 or 2.

R represents a lower alkyl group, a lower alkoxy group or a lower haloalkyl group; preferably a lower alkyl group having 1 to 3 carbon atoms, a methoxy group or a lower haloalkyl group having 1 to 2 carbon atoms and 1 to 5 fluorine atoms; more preferably a lower alkyl group having 1 to 2 carbon atoms, a methoxy group or a difluoromethyl group. W represents a hydroxyl group or a halogen atom, preferably a hydroxyl group or a bromine atom.

Z represents a halogen atom, a lower alkylsulfonyloxy group which may be substituted, or a phenylsulfonyloxy group which may be substituted; preferably a chlorine atom, a bromine atom, an iodine atom, a lower alkylsulfonyloxy group having 1 to 4 carbon atoms which may be substituted by one or more halogen atoms, or a phenylsulfonyloxy group which may be substituted by a halogen atom, a lower alkyl group, a lower haloalkyl group, a lower alkoxy group or a lower haloalkoxy group; more preferably a bromine atom, an iodine atom, a lower alkylsulfonyloxy group having 1 to 2 carbon atoms which may be substituted by 1 to 5 halogen atoms (particularly preferably a methanesulfonyloxy group which may be substituted by 1 to 3 fluorine atoms or chlorine atoms), or a phenylsulfonyloxy group which may be substituted by a halogen atom or a lower alkyl group (particularly preferably a phenylsulfonyloxy group which may be substituted by a methyl group).

The compound according to the present invention represented by the general formula (I) can be synthesized, for example, in accordance with the following reactions (1) to (4).

wherein Z¹ represents a halogen atom and A, B and R are the same as defined above.

The above reaction is an addition reaction of a hypohalous acid to the double bond, namely, a halohydrin formation reaction of an olefin compound. This reaction is effectively carried out by reacting an alkaline metal salt of a hypohalous acid, an alkaline metal salt of a hypohalous acid, an N-halogenosuccinimide, chlorine, bromine, iodine, etc. with the compound (II) in water or an aqueous solvent in the presence or absence of an acid and/or an oxidizing agent. As a solvent for the aqueous solvent, alcohols, tetrahydrofuran, dimethylsulfoxide, etc. are mentioned. As the acid and oxidizing agent, various kinds of acid and oxidizing agent which are generally used in the addition reaction of a hypohalous acid to a double bond may be used. As the example for the acid, mineral acids and aliphatic acids such as acetic acid may be mentioned, and mercuric acetate, marcuric oxide, etc. may be mentioned as the example for the oxidizing agent. The reaction temperature is −30° to 100° C., preferably −10° to 60° C., and the reaction time is ordinarily 0.1 to 24 hours, preferably 0.5 to 6 hours.

The intermediate (II) is obtained, for example, by the following reaction.

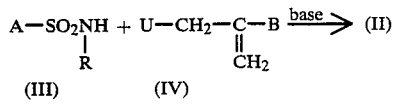

or

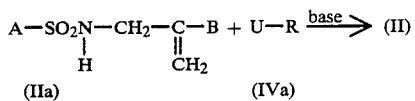

wherein U represents a halogen atom and A, B and R are the same as defined above.

These alkylations can be conducted by reacting a sulfonamide with a halide in a two-phase system of aqueous alkali metal hydroxide and organic solvent in the presence of a phase transfer catalyst. The phase transfer catalyst used in the above alkylation includes various kinds of compounds such as benzyltrialkylammonium halides, tetraalkylammonium halides, methyltrialkylammonium halides, alkyltrimethylammonium halides, (hydroxyalkyl)trimethylammonium halides, tetraalkylammonium bisulfates, etc. More precisely, benzyltrimethyl(ethyl)ammonium chloride(bromide), tetra-n-butylammonium chloride (bromide, or iodide), methyltrioctyl(decyl)ammonium chloride, etc. may be mentioned. The phase transfer catalyst may be used in an amount of 1/5 to 1/250 mol equivalent, preferably 1/50 to 1/100 mol equivalent based on the amount of the sulfonamide as the starting substance.

The aqueous alkali metal hydroxide includes an aqueous sodium hydroxide, an aqueous potassium hydroxide, etc., and the concentration of the aqueous alkali metal hydroxide is preferably 35 to 60%.

As the organic solvent, aprotic solvents such as benzene, toluene, xylene, cyclohexane, cycloheptane and dichloromethane may be exemplified.

The reaction temperature is 10° to 100° C., preferably 40° to 80° C., and the reaction time is 0.5 to 24 hours, preferably 1 to 6 hours.

The above alkylations can be also conducted by another different way in which a sulfonamide is reacted with a halide in an aprotic solvent such as N,N-dimethylformamide, N-methylpyrrolidone, dimethylsulfoxide, acetonitrile, tetrahydrofuran, dioxane, 1,2-dimethoxyethane, etc. in the presence of a base such as sodium hydride, potassium hydride, sodium metal, potassium metal, sodium carbonate, potassium carbonate at a temperature of −20° to 100° C., preferably −10° to 80° C. for 0.5 to 24 hours, preferably 0.5 to 6 hours.

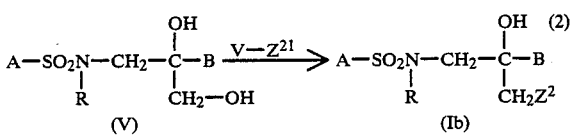

(2)

wherein V represents a halogen atom or a sulfonyloxy group which corresponds to a sulfonyl group defined in $Z^{21}$, $Z^{21}$ represents a lower alkylsulfonyl group which may be substituted or a phenylsulfonyl group which may be substituted, and $Z^2$ represents a lower alkylsulfonyloxy group which may be substituted or a phenylsulfonyloxy group which may be substituted.

The above sulfonylation reaction is carried out without a solvent or in a solvent in the presence or absence of a base. When a solvent is used, as an appropriate solvent, for example, N,N-dimethylformamide, N-methylpyrrolidone, tetrahydrofuran, dioxane, 1,2-dimethoxyethane, benzene, toluene, ethyl acetate, methylene chloride and chloroform will be cited. As the base, pyridine, triethylamine, N,N-dimethylaniline, N,N-diethylaniline, sodium (or potassium) bicarbonate, sodium (or potassium) carbonate, sodium (or potassium) hydroxide and sodium hydride are usable. The reaction temperature is −20° to 100° C., preferably 0° to 60° C., and the reaction time is ordinarily 1 to 24 hours.

The intermediate (V) is obtained, for example, by the following reaction.

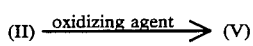 (a)

The above reaction is classified as the oxidation reaction of olefins to 1,2-diols. This reaction is described in many publications such as, for example, Alan H. Haines, "Methods for the Oxidation of Organic Compounds", pp. 73 to 93 (1985), ACADEMIC PRESS. For example, the intermediate (V) can be obtained by reacting a mixture of the intermediate (II), hydrogen peroxide and an aliphatic acid such as formic acid, acetic acid, etc. at a temperature of 0° to 100° C., preferably 20° to 60° C. for 0.5 to 24 hours, preferably 1 to 12 hours, and then treating with an aqueous alkali such as sodium hydroxide at a temperature of 0° to 100° C., preferably 20° to 60° C. (b)

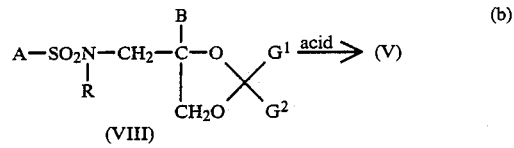

wherein $G^1$ represents a hydrogen atom or a lower alkyl group, $G^2$ represents a phenyl group which may be substituted or a lower alkyl group, and A, B and R are the same as defined above.

This reaction is conducted by treating the compound (VIII) in a solvent or a mixed solvent of water, lower alcohols such as methanol, ethanol, etc., cyclic ethers such as tetrahydrofuran, dioxane, etc. in the presence of an acid such as formic acid, acetic acid, hydrochloric acid, sulfuric acid, sulfonic acid, etc. at a temperature of −20° to 100° C., preferably 10° to 60° C. for 0.5 to 12 hours, preferably 1 to 6 hours.

The protected compound (VIII) is obtained in accordance with the following reaction formula:

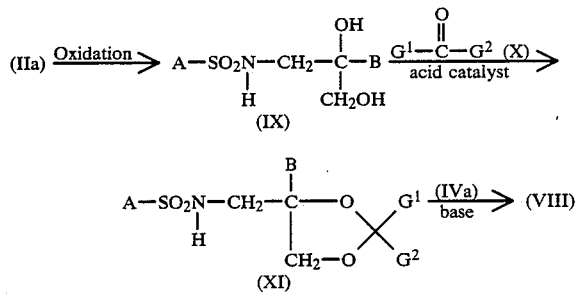

wherein A, B, $G^1$ and $G^2$ are the same as defined above.

The reaction of (IIa)→(IX) can be conducted by a similar way to the procedure for the reaction of (II)→(V) described above.

The compound (IX) is converted to the compound (XI) by usually refluxing a solution of the compound (IX) in an aromatic hydrocarbon such as benzene, toluene, xylene, etc. in the presence of a sulfonic acid such as p-toluenesulfonic acid, etc. or a mineral acid such as sulfuric acid, etc. for 1 to 36 hours, preferably 1 to 18 hours, while using, if occasion requires, an apparatus for dehydrating reaction such as Dean-Stark trap.

The reaction of (XI)→(VIII) can be conducted by a similar way to the procedure for the reaction of (III)+(IV)→(II) or (IIa)+(IVa)→(II) described above.

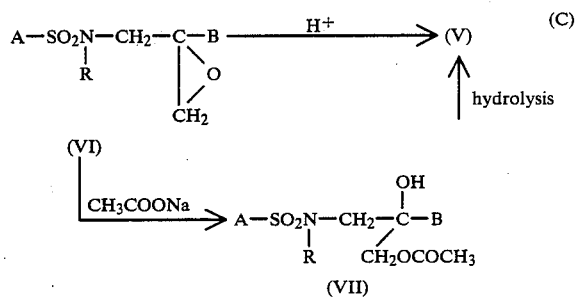

wherein A, B and R are the same as defined above.

The reaction of (VI)→(V) can be conducted by treating the compound (VI) in water or an aqueous solvent containing lower alcohols such as methanol, ethanol, etc., cyclic ehters such as tetrahydrofuran, dioxane, etc., and the like in the presence of an acid such as hydrochloric acid, hydrobromic acid, sulfuric acid, etc. at a temperature of $-10°$ to $100°$ C., preferably $10°$ to $80°$ C. for 1 to 100 hours, preferably 2 to 48 hours.

The reaction of (VI)→(VII)→(V) can be conducted as follows. First, the compound (VII) can be obtained by reacting the compound (VI) with anhydrous sodium acetate in an aprotic solvent such as N,N-dimethylformamide, N-methylpyrrolidone, etc., a lower aliphatic acid or a lower alcohol at a temperature of $10°$ to $200°$ C., preferably $30°$ to $40°$ C. for 1 to 36 hours, preferably 2 to 24 hours. Then, the thus obtained compound (VII) can be hydrolyzed to the compound (V) by treating in water or an aqueous solvent containing a lower alcohol or a cyclic ether in the presence of a base such as sodium(potassium) hydroxide, sodium(potassium) carbonate, triethylamine, etc. at a temperature of $-20°$ to $100°$ C., preferably $10°$ to $50°$ C. for 0.5 to 10 hours, preferably 1 to 6 hours.

The epoxide (VI) is easily obtained in accordance with the following reaction formula:

$$(II) \xrightarrow{\text{oxidizing agent}} (VI)$$

or

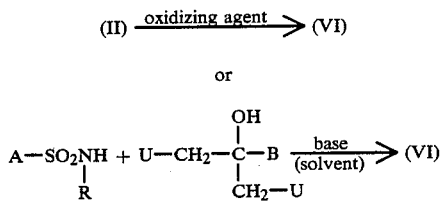

wherein A, B, R and U are the same as defined above.

The above oxidation reaction of (II)→(VI) can be conducted by the action of an oxidizing agent on the compound (II) in a solvent such as chloroform, dichloromethane, carbon tetrachloride, water, etc. As the oxidizing agent, m-chloroperbenzoic acid, peracetic acid, hydrogen peroxide, etc. may be mentioned. These oxidizing agent can be used solely or in combination with a various kind of buffer agent for preventing byreaction or stabilizing the product. The reaction temperature is $-20°$ to $100°$ C., preferably $10°$ to $90°$ C., and the reaction time is 1 to 24 hours, preferably 2 to 12 hours.

The other reaction of the above can be conducted without or in a solvent. As suitable solvents, aprotic solvent such as N,N-dimethylformamide, N-methylpyrrolidone, dimethylsulfoxide, acetonitrile, tetrahydrofuran, dioxane, 1,2-dimethoxyethane, etc. may be exemplified. As the base, sodium(potassium) hydride, sodium(potassium) hydroxide, sodium(potassium) metal, sodium(potassium) carbonate, etc. may be exemplified. The reaction temperature is $-20°$ to $100°$ C., preferably $-10°$ to $60°$ C., and the reaction time is 0.5 to 24 hours, preferably 0.5 to 12 hours.

This reaction can be also conducted in the presence of a phase transfer catalyst by a similar way to the procedure for the reaction of (III)+(IV)→(II) or (IIa)+-(IVa) (II) described above.

The reaction between the epoxide (VI) and a hydrogen halide or a sulfonic acid is carried out by reacting a hydrogen halide or a sulfonic acid with compound (VI) in a solvent or mixed solvent of water, diethyl ether, diisopropyl ether, tetrahydrofuran, dioxane, benzene, toluene, dichloromethane, chloroform, carbon tetrachloride, N,N-dimethylformamide, N-methylpyrrolidone, ethyl acetate, 2-propanol, 2-methyl-2-propanol, etc. in the presence or absence of an organic base such as pyridine, picoline, quinoline, etc. or inorganic base such as sodium(potassium) hydroxide, etc. The reaction temperature is $-120°$ to $150°$ C., preferably $-60°$ to $80°$ C., and the reaction time is 0.1 to 48 hours, ordinarily 0.5 to 12 hours.

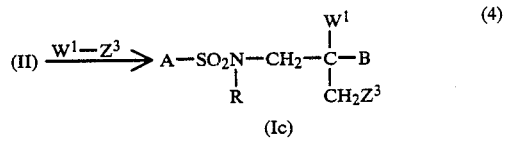

wherein $W^1$ and $Z^3$ each represent a halogen atom.

The above reaction is the addition reaction of halogen to the olefin (II) and is carried out in a suitable inert solvent such as chloroform, carbon tetrachloride, dichloroethane, etc. at a temperature of $-50°$ to $150°$ C., ordinarily $0°$ to $50°$ C.

The compound of the present invention obtained in the above-described way has optical isomers. Therefore, the compound of the present invention is usually obtained in the form of a racemate, but it is possible to obtain each enantiomer by a known method such as asymmetric synthesis. The compound of the present invention is usable as a herbicide either in the form of a racemate or each enantiomer.

When the compound of the present invention is applied to a herbicidal composition, the compound may be used as it is, or in the form of wettable powder, granules, emulsifiable concentrate or flowable produced by an ordinary method using an appropriate carrier, surfactant or the like. As the carrier and surfactant, for example, those described in Japanese Patent Application Laid-Open (KOKAI) No. 60-25986 (1985) are usable. Also, a herbicidal composition containing the compound of the present invention may contain other agricultural chemical used in the same field, e.g., an insecticide, fungicide, herbicide, growth regulating agent, and a fertilizer.

The amount of the compound according to the present invention used in field is different depending upon the kind of the compound used, weed to be treated, treating time, treating method and the nature of the soil, but ordinarily, the preferable amount is 0.25 to 40 g/a, preferably 1 to 20 g/a per are.

A slight change is observed in the physiological activity of the compound of the present invention in accordance with the kind of a functional group and the position of substitution, but any compound of the present invention has a very strong herbicidal activity on Echinochloa crus-galli, which is the most harmful weed to paddy-rice plants, from preemergence to an advanced stage of growing, and causes little damage to paddy-rice plants.

The herbicidal spectrum of the compound of the present invention is the highest to Echinochloa crusgalli. The compound of the present invention is also effective to weeds of Cyperaceae such as Cyperus difformis, Scripus Juncoides and Eleocharis acicularis and annual broadleaf weeds such as Rotala indica and Monochoria vaginalis, and has a high sensitivity to Cyperus serotinus, which is a strongly harmful perennial weed.

The compound of the present invention is effective in a low dosage as a herbicidal active ingredient to various kinds of weeds from preemergence to an advanced stage of growing, and has a wide application time in which the compound is preferably used. In addition, a compound of the present invention has a herbicidal activity under not only the paddy condition but also the upland condition.

The activity of the compound of the present invention on annual broadleaf weeds and perennial broadleaf weeds such as Sagittaria pygmaea in an advanced growing stage is slightly low, but by mixing the compound with a herbicide which is effective to these weeds, it is possible to greatly enlarge the width of the herbicidal spectrum and to increase the herbicidal effect. Such a herbicide may be mixed with the present compound at a ratio of 0.1~1000 g, preferably 1~500 g, to 100 g of the present compound.

In this case, the following will be cited as examples of preferred herbicides mixed with the composition of the present invention:

Pyrazole herbicide:
4-(2,4-dichlorobenzoyl)-1,3-dimethylpyrazol-5-yl p-toluenesulfonate,
4-(2,4-dichlorobenzoyl)-1,3-dimethyl-5-phenacyloxypyrazole,
4-(2,4-dichloro-3-methylbenzoyl)-1,3-dimethyl-5-(methylphenacyloxy)pyrazole,
4-(2,4-dichlorobenzoyl)-1-methyl-5-phenacyloxypyrazole.

Sulfonylurea herbicide:
methyl 2-(4,6-dimethoxypyrimidin-2-ylcarbamoylaminosulfonylmethyl)benzoate, ethyl 5-(4,6-dimethoxypyrimidin-2-ylcarbamoylaminosulfonyl)-1-methylpyrazole-4-carboxylate.

Phenoxy herbicide:
2,4-dichlorophenoxyacetic acid and a derivative thereof, 4-chloro-2-methylphenoxyacetic acid and a derivative thereof, 4-(4-chloro-2-methylphenoxy)-butyric acid and a derivative thereof, S-ethyl 4-chloro-2-methylphenoxythioacetate, 2-(2-naphthoxy)propionanilide, 2-(2,4-dichloro-3-methylphenoxy)-propionanilide, butyl 2-[4-(5-trifluoromethyl-2-pyridyloxy)phenoxy propionate.

Haloacetanilide herbicide:
2-chloro-2',6'-diethyl-N-butoxymethylacetanilide, 2-chloro-2',6'-diethyl-N-propoxyethylacetanilide, ethyl N-chloroacetyl-N-(2,6-diethylphenyl)aminoacetate.

Acid amide herbicide:
3',4'-dichloropropionanilide,
2',3'-dichloro-4-ethoxymethoxybenzanilide,
2-bromo-3,3-dimethyl-N-(α,α-dimethylbenzyl)-butanamide,
2-benzothiazol-2-yloxy-N-methylacetanilide,
2',4'-difluoro-2-(3-trifluoromethylphenoxy)nicotinic acid anilide.

Carbamate herbicide:
S-(4-chlorobenzyl)-N,N-diethylthiolcarbamate, S-ethyl-N,N-hexamethylenethiolcarbamate, N,N-hexamethylene-S-isopropylthiolcarbamate, S-benzyl-N-ethyl-N-(1,2-dimethylpropyl)thiolcarbamate, S-(1-methyl-1-phenetyl)piperidine-1-carbothioate, O-(3-t-butylphenyl)-N-(6-methoxypyridin-2-yl)-N-methylthiocarbamate.

Urea herbicide:
1-(α,α-dimethylbenzyl)-3-(4-methylphenyl)urea, 3-(benzothiazol-2-yl)-1,3-dimethylurea, 3-(3,4-dichlorophenyl)-1-methoxy-1-methylurea, 3-(3,4-dichlorophenyl)-1,1-dimethylurea, 3-[4-(4-methylphenetyloxy)phenyl]-1-methoxy-1-methylurea, 1-(2-substituted benzyl)-3-(1,1-dimethylbenzyl)urea.

Diphenyl ether herbicide:
2,4,6-trichloro-4'-nitrodiphenyl ether, 2,4-dichloro-3'-methoxy-4'-nitrodiphenyl ether, methyl 5-(2,4-dichlorophenoxy)-2-nitrobenzoate, 3-[5-(2-chloro-4-trifluoromethylphenoxy)-2-nitrophenoxytetrahydrofuran.

Triazine herbicide:
2-chloro-4-ethylamino-6-isopropylamino-1,3,5-triazine, 2,4-bis(ethylamino)-6-methylthio-1,3,5-triazine, 2-ethylamino-4-(1,2-dimethylpropylamino-6-methylthio-1,3,5-triazine,
2,4-bis(isopropylamino)-6-methylthio-1,3,5-triazine,
4-amino-6-t-butyl-3-methylthio-1,2,4-triazin-5(4H)-one.

Dinitroaniline herbicide:
2,6-dinitro-N,N-dipropyl-4-trifluoromethylaniline,
N-(1-ethylpropyl)-3,4-dimethyl-2,6-dinitroaniline, 3,5-dinitro-N,N-dipropylsulfanilamide.

Nitrile herbicide:
4-hydroxy-3,5-diiodobenzonitrile, 3,5-dibromo-4-hydroxybenzonitrile, 2,6-dichlorobenzonitrile.

Phosphorus-containing herbicide:
O-ethyl-O-(5-methyl-2-nitrophenyl)-N-sec-butyl phosphoroamidate, S-(2-benzenesulfonylaminoethyl)-O,O-diiso-propylphosphorodithioate, S-(2-methylpiperidin-1-yl)carbonylmethyl-O,O-dipropylphosphorodithioate, N-(phosphonomethyl)glycine, ammonium (3-amino-3-carboxy)propylmethylphosphinate, sodium (2-amino-4-methylphosphino)-butyrylalanylalaninate.

Quaternary ammonium salt herbicide:
1,1'-ethylene-2,2'-pipyridylium dibromide, 1,1'-dimethyl-4,4'-bipyridylium dichloride.

Other herbicides:
3,6-dichloro-2-methoxybenzoic acid, 3,7-dichloroquinoline-8-carboxylic acid, pentachlorophenol, 2-sec-butyl-4,6-dinitrophenol, 2-amino-3-chloro-1,4-naphthoquinone, 1,2-dihydropyridazine-3,6-dione, 3-(2-methylphenoxy)pyridazine, 3-isopropyl-1H-2,1,3-benzothiazin-4(3H)-one 2,2-dioxide, 2,2-dichloropropionic acid, 2,2,3,3-(tetrafluoropropionic acid, methyl 6-(4-isopropyl-4-methyl-5-oxo-2-imidazolin-2-yl)-3(4)-methylbenzoate, 2-(4-isopropyl-4-methyl-5-oxo-2-imidazolin-2-yl)nicotinic acid and a salt thereof, 2-(4-isopropyl-4-methyl-5-oxo-2-imidazolin-2-yl)quinoline-3-carboxylic acid, 1-methyl-4(1-methylethyl)-2-(2-methylphenylmethoxy)-7-oxabicyclo[2,2,1]heptane, 1-(3-methylphenyl)-5-phenyl-1H-1,2,4-triazole-3-carboxamide, 2-(N-ethoxybutylimidoyl)- 5-(2-ethylthiopropyl)-3-hydroxy-2-cyclohexen-1-one, 2-(3,5-dichlorophenyl)-2-(2,2,2-trichloroethyl)oxirane, N-[4-(4-chlorobenzyloxy)-phenyl]-3,4,5,6-tetrahydrophthalimide, N-(4-chloro-2-fluoro-5-propargyloxyphenyl)-3,4,5,6-tetrahydrophthalimide, 3-(2,4-dichloro-5-isopropoxyphenyl)-5-t-butyl-1,3,4-oxadiazol-2-(3H)-one, 4-methoxy-3,3'-dimethylbenzophenone, 2-ethoxy-2,3-dihydro-3,3-dimethyl-5-benzofuranylmethane sulfonate,1-methyl-3-phenyl-5-(3-trifluoromethylphenyl)pyridine-4(1H) one.

These may be used in the form of mixture.

The present invention will be explained in more detail with reference to the following non-limitative examples.

REFERENCE EXAMPLE 1

Preparation of 4-fluoro-N-methyl-N-(2-phenyl-2-propenyl)-benzenesulfonamide

To a mixture of 5.0 g of 4-fluoro-N-methyl-benzenesulfonamide, 5.8 g of α-(bromomethyl)styrene, 0.17 g of tetra-n-butylammonium bromide and 15 ml of toluene, 10 ml of 50% aqueous sodium hydroxide was added. The mixture was stirred at 80° C. for 2 hours. After cooling, the solution was extracted with 60 ml of ethyl acetate, and the organic layer was washed with water, dried over anhydrous sodium sulfate and concentrated. The residue was purified by silica gel column chromatography (developing solvent:ethyl acetate - n-hexane) to obtain 6.8 g of the intitled compound.

IR spectrum (KBr) cm$^{-1}$: 3060, 1595, 1500, 1465, 1340, 1300, 1240, 1165.

$^1$H—NMR spectrum (CDCl$_3$—TMS)δ: 2.60 (3H, s), 4.05 (2H, s), 5.20 (1H, s), 5.50 (1H, s), 7.15 to 7.50 (7H, m), 7.80 (2H, dd).

REFERENCE EXAMPLE 2

Preparation of 4-cyano-N-methyl-N-(2-phenyl-2-propenyl)benzenesulfonamide

To a mixture of 2.30 g of 4-cyano-N-methylbenzenesulfonamide, 2.40 g of α-(bromomethyl)styrene and 20 ml of N,N-dimethylformamide, 0.63 g of 50% sodium hydride (oil dispersed) was slowly added with stirring under ice cooling, then the mixture was stirred at room temperature for 6 hours. After evaporating the solvent under a reduced pressure, ethyl acetate was added to the residue. The organic layer was washed with water and dried over anhydrous sodium sulfate. After distilling off the solvent, the residue was purified by silica gel column chromatography (developing solvent: ethyl acetate n-hexane) to obtain 1.70 g of the titled compound.

IR spectrum (KBr) cm$^{-1}$: 3100, 2925, 2220, 1460, 1340, 1160.

NMR spectrum (CDCl$_3$—TMS)δ: 2.65 (3H, s), 4.10 (2H, s), 5.22 (1H, s), 5.50 (1H, s), 7.38 (5H, m), 7.82 (4H, s).

REFERENCE EXAMPLE 3

Preparation of N-difluoromethyl-4-methyl-N-(2-phenylpropen-3-yl)benzenesulfonamide A mixture of 1.24 g of 4-methyl-N-(2-phenyl-2-propenyl) benzenesulfonamide, 1.24 g of sodium hydroxide, 1.24 g of tetra-n-butylammonium bromide and 40 ml of cyclohexane was refluxed with stirring. Chlorodifuloromethane was passed through the mixture for 1 hour. After cooling, the reaction mixture was diluted with water and was extracted with ether. The organic layer was dried over anhydrous sodium sulfate and the solvent was distilled off. The residue was purified by silica gel column chromatography (developing solvent:ethyl acetate -n-hexane (1:5)) to obtain 0.92 g of the titled compound.

IR spectrum (neat) cm$^{-1}$: 1360, 1160, 1110, 1090, 1015.

$^1$H—NMR spectrum (CDCl$_3$—TMS)δ: 2.45 (3H, s), 4.24 (2H, s), 5.36, 5.42 (each 1H, s), 7.09 (1H, t), 7.30, 7.70 (each 2H, d), 7.33 (5H, s).

The compounds synthesized in accordance with Reference Examples 1 to 3 are shown in Table 1.

TABLE 1

$$A-SO_2N(R)-CH_2-C(=CH_2)-B \quad (II)$$

| A | B | R | Physical Constant |
|---|---|---|---|
| phenyl | phenyl | CH$_3$ | mp 109~111° C. |
| 2-Cl-phenyl | phenyl | CH$_3$ | n$_D^{26}$ 1.5937 |
| 2-CH$_3$-phenyl | phenyl | CH$_3$ | n$_D^{26}$ 1.5812 |
| 2-CF$_3$-phenyl | phenyl | CH$_3$ | mp 55~56° C. |

TABLE 1-continued $$A-SO_2N(R)-CH_2-C(=CH_2)-B \quad (II)$$

| A | B | R | Physical Constant |
|---|---|---|---|
| 2-CF$_3$-C$_6$H$_4$- | 3-Cl-C$_6$H$_4$- | CH$_3$ | $n_D^{25}$ 1.5581 |
| 3-Cl-C$_6$H$_4$- | C$_6$H$_5$- | CH$_3$ | mp 74~75° C. |
| 3-CH$_3$-C$_6$H$_4$- | C$_6$H$_5$- | CH$_3$ | mp 92~94° C. |
| 3-CF$_3$-C$_6$H$_4$- | C$_6$H$_5$- | CH$_3$ | mp 69~70° C. |
| 3-O$_2$N-C$_6$H$_4$- | C$_6$H$_5$- | CH$_3$ | mp 59~60° C. |
| 4-F-C$_6$H$_4$- | C$_6$H$_5$- | CH$_3$ | mp 80~81° C. |
| 4-Cl-C$_6$H$_4$- | C$_6$H$_5$- | CH$_3$ | mp 127~128° C. |
| 4-Br-C$_6$H$_4$- | C$_6$H$_5$- | CH$_3$ | mp 142~143° C. |
| 4-Br-C$_6$H$_4$- | C$_6$H$_5$- | C$_2$H$_5$ | mp 104~105° C. |
| 4-I-C$_6$H$_4$- | C$_6$H$_5$- | CH$_3$ | mp 130~132° C. |
| 4-CH$_3$-C$_6$H$_4$- | C$_6$H$_5$- | CH$_3$ | mp 75~77° C. |

TABLE 1-continued $$A-SO_2\underset{R}{N}-CH_2-\underset{\underset{CH_2}{\|}}{C}-B \qquad (II)$$

| A | B | R | Physical Constant |
|---|---|---|---|
| 4-CH₃-C₆H₄- | 3-CF₃-C₆H₄- | CH₃ | mp 69~70° C. |
| 4-CH₃-C₆H₄- | C₆H₅- | OCH₃ | mp 99.5~100.5° C. |
| 4-CH₃-C₆H₄- | C₆H₅- | CHF₂ | $n_D^{24}$ 1.5580 |
| 4-nC₃H₇-C₆H₄- | C₆H₅- | CH₃ | mp 53.5~54.5° C. |
| 4-nC₃H₇O-C₆H₄- | C₆H₅- | CH₃ | mp 75.5~77° C. |
| 4-CF₃-C₆H₄- | C₆H₅- | CH₃ | mp 123~125° C. |
| 4-NC-C₆H₄- | C₆H₅- | CH₃ | mp 115.5~117° C. |
| 2,4-(CH₃)₂-C₆H₃- | C₆H₅- | CH₃ | mp 47~49° C. |
| 4-Cl-2-CF₃-C₆H₃- | C₆H₅- | CH₃ | $n_D^{24}$ 1.5605 |
| 2,5-(CH₃)₂-C₆H₃- | C₆H₅- | CH₃ | mp 59~61° C. |
| 2-CH₃-4-i-C₃H₇-C₆H₃- | C₆H₅- | CH₃ | $n_D^{25}$ 1.5650 |

TABLE 1-continued $$A-SO_2N-CH_2-C-B \quad (II)$$
$$\phantom{A-SO_2N-}\overset{|}{R}\phantom{-CH_2-}\overset{\|}{CH_2}$$

| A | B | R | Physical Constant |
|---|---|---|---|
| 3,4-dichlorophenyl | phenyl | $CH_3$ | mp 83~84° C. |
| 2-methyl-4-chlorophenyl (CH₃ up, Cl down) | phenyl | $CH_3$ | mp 112.5~114° C. |
| 2-methyl-4-chlorophenyl | phenyl | $CHF_2$ | mp 73~74° C. |
| 2,3-dimethylphenyl | phenyl | $CH_3$ | mp 89~90° C. |
| 3-methyl-4-cyanophenyl | phenyl | $CH_3$ | mp 125~127° C. |
| indanyl | phenyl | $CH_3$ | mp 89~90° C. |
| 5,6,7,8-tetrahydronaphthyl | phenyl | $CH_3$ | mp 115~116° C. |
| 5,6,7,8-tetrahydronaphthyl | phenyl | $CHF_2$ | mp 71~72° C. |
| 2,3-dihydrobenzofuranyl | phenyl | $CH_3$ | mp 126~127° C. |
| 2,4,5-trimethylphenyl | phenyl | $CH_3$ | mp 91~91.5° C. |

REFERENCE EXAMPLE 4

Preparation of 2,5-dimethyl-N-methyl-N-(2,3-epoxy2-phenylpropyl)benzenesulfonamide After dissolving 3.0 g 2,5-dimethyl-N-methyl-N-(2-(phenyl 2-propenyl)-benzenesulfonamide in 30 ml of chloroform, were added 0.70 g of sodium acetate trihydrate and 5.3 ml of 40% peracetic acid and stirred at 60° C. for 3 hours. The reaction mixture was washed subsequently with 10% aqueous sodium bisulfite, 10% aqueous sodium carbonate and water, dried over anhydrous sodium sulfate and concentrated under a reduced pressure. The residue was purified by silica gel column chromatography (developing solvent:ethyl acetate -n-hexane) to obtain 2.5 g of the titled compound.

IR spectrum (KBr) cm$^{-1}$: 3040, 2975, 1330, 1165.

$^1$H—NMR spectrum (CDCl$_3$—TMS)$\delta$: 2.35 (3H, s), 2.36 (3H, s), 2.72 (1H, d), 2.83 (3H, s), 3.07 (1H, d), 3.34 (1H, d), 4.08 (1H, d), 7.0 to 7.5 (7H, m), 7.65 (1H, m).

REFERENCE EXAMPLE 5

Preparation of N-methyl-N-(2,3-epoxy-2-phenylpropyl)-p-toluenesulfonamide

A mixture of 9.8 g of N-methyl-N-(2-phenyl-2-propenyl)-p-toluenesulfonamide, 9.63 g of m-chloroperbenzoic acid and 280 ml of chloroform were stirred at 60° C. for 3 hours. After cooling, the reaction mixture was washed subsequently with 10% aqueous sodium bisulfite and water, dried over anhydrous magnesium sulfate. The solvent was distilled off and the residue was purified by silica gel column chromatography (developing solvent:ethyl acetate -n-hexane) to obtain 7.7 g of the titled compound.

IR spectrum (KBr) cm$^{-1}$: 3050, 2980, 1595, 1450, 1345, 1165.

$^1$H—NMR spectrum (CDCl$_3$—TMS)$\delta$: 2.44 (3H, s), 2.74 (3H, s), 2.76 (1H, d), 3.09 (1H, d), 3.15 (1H, d), 4.01 (1H, d), 7.2 to 7.7 (9H, m).

REFERENCE EXAMPLE 6

Preparation of N-[2-(3-chlorophenyl)-2,3-epoxypropyl]-4-cyano-N-methylbenzenesulfonamide To a mixture of 10.0 g of 4 cyano-N-methyl benzenesulfonamide and 100 ml of 1,2-dimathoxyethane, 3.5 g of 60% oil dispersed sodium hydride was slowly added under stirring. After 20-minute stirring, the mixture was cooled with ice bath. To the mixture, was slowly added 16.1 g of 2-chloromethyl-2-(3-chlorophenyl)oxirane then the temperature was restored to room temperature followed by reflux for 7 hours. After cooling, the insoluble matter was filtered off, and the filtrate was concentrated under a reduced pressure The residue was purified by silica gel column chromatography (developing solvent:ethyl acetate -n-hexane) to obtain 11.5 g of the titled compound.

IR spectrum (KBr) cm$^{-1}$: 3095, 2240, 1345, 1160, 1135, 1085.

$^1$H—NMR spectrum (CDCl$_3$—TMS)$\delta$: 2.72 (1H, d), 2.80 (3H, s), 3.03 (1H, d), 3.14 (1H, d), 4.19 (1H, d), 7.32 (4H, m), 7.82 (4H, s).

REFERENCE EXAMPLE 7

Preparation of N-[2-(3-chlorophenyl) 2,3-epoxypropyl]-N-methyl p-toluenesulfonamide To a mixture of 0.88 g of N-methyl-p-toluenesulfonamide, 1.04 g of 2 (3-chlorophenyl)-3-dichloro-2-propanol and 5 ml of N,N-dimethylforamide, 0.19 g of sodium hydride was slowly added under stirring. After 4 hour stirring, the insoluble matter was filtered off, and the filtrate was concentrated under a reduced pressure. The residue was purified by silica gel column chromatography (developing solvent:ethyl acetate -n-hexane) to obtain 0.32 g of the intended compound.

IR spectrum (KBr) cm$^{-1}$: 3060, 1335, 1165, 1160.

$^1$H—NMR spectrum (CDCl$_3$—TMS)$\delta$: 2.46 (3H, s), 2.68 (1H, d), 2.75 (3H, s), 3.09 (1H, d), 3.10 (1H, d), 4.05 (1H, d), 7.20 to 7.45 (6H, m), 7.50 to 7.70 (2H, m).

REFERENCE EXAMPLE 8

Preparation of 4-bromo-N [2 (3-chlorophenyl).2,3-epoxypropyl]-N-methylbenzenesulfonamide To a mixture of 2.0 g of 4-bromo-N-methyl benzenesulfonamide, 1.9 g of 2 (3-chlorophenyl)-1,3-dichloro 2-propanol, 0.05 g of tetra.n.butylammonium bromide and 5 ml of toluene, was added 5 ml of 40% aqueous sodium hydroxide. The mixture was stirred at 80° C. for 7 hours. After cooling, the reaction mixture was extracted with ethyl acetate, and the organic layer was washed with water, dried over anhydrous sodium sulfate and concentrated under a reduced pressure. The residue was purified by silica gel column chromatography (developing solvent:ethyl acetate -n-hexane) to obtain 1.02 g of the intended compound.

IR spectrum (KBr) cm$^{-1}$: 3070, 1340, 1165, 1155.

$^1$H—NMR spectrum (CDCl$_4$—TMS)$\delta$: 2.76 (3H, s), 2.76 (1H, d), 3.06 (1H, d), 3.09 (1H, d), 4.12 (1H, d), 7.15 to 7.50 (4H, m), 7.67 (4H, s).

The compounds prepared in accordance with Reference Examples 4 to 8 are shown in Table 2.

TABLE 2

$$A-SO_2N-CH_2-C-B \quad (VI)$$
$$\underset{R}{|} \quad \underset{CH_2}{\overset{\diagdown}{\underset{\diagup}{O}}}$$

| A | B | R | Physical Constant |
|---|---|---|---|
| phenyl | phenyl | CH$_3$ | mp 102~104° C. |

TABLE 2-continued
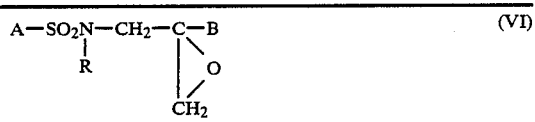
| A | B | R | Physical Constant |
|---|---|---|---|
| 2-Cl-C6H4 | C6H5 | CH3 | mp 69.5~71° C. |
| 2-CH3-C6H4 | C6H5 | CH3 | mp 95~98° C. |
| 2-CF3-C6H4 | C6H5 | CH3 | mp 78~79° C. |
| 2-CF3-C6H4 | 3-Cl-C6H4 | CH3 | mp 77~78° C. |
| 3-Cl-C6H4 | C6H5 | CH3 | mp 71~72.5° C. |
| 3-CH3-C6H4 | C6H5 | CH3 | mp 107~109° C. |
| 4-F-C6H4 | C6H5 | CH3 | mp 105~106° C. |
| 4-Cl-C6H4 | C6H5 | CH3 | mp 121~123° C. |
| 4-Cl-C6H4 | 3-Cl-C6H4 | CH3 | mp 81~83° C. |
| 4-Cl-C6H4 | 3-n-C3H7-C6H4 | CH3 | mp 103.5~104° C. |
| 4-Br-C6H4 | C6H5 | CH3 | mp 107.5~108° C. |

TABLE 2-continued
$$A-SO_2N(R)-CH_2-C(B)(CH_2O) \quad (VI)$$
| A | B | R | Physical Constant |
|---|---|---|---|
| 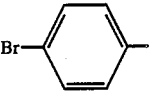 | 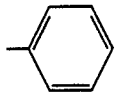 | $C_2H_5$ | mp 104~105° C. |
| 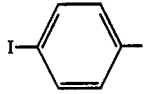 | 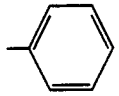 | $CH_3$ | mp 100~104° C. |
| 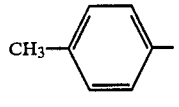 | 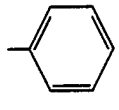 | $CH_3$ | mp 110.5~112.5° C. |
| 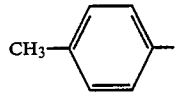 | 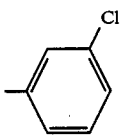 | $CH_3$ | mp 87~89° C. |
| 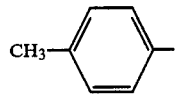 | 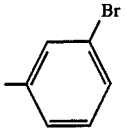 | $CH_3$ | mp 105~106° C. |
| 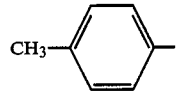 | 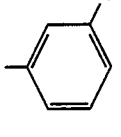 | $CH_3$ | mp 110~111° C. |
| 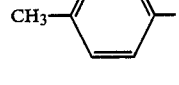 | 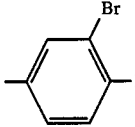 | $CH_3$ | mp 91~92° C. |
| 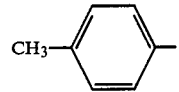 | 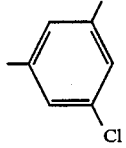 | $CH_3$ | mp 109~111° C. |
| 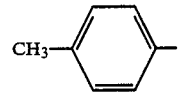 | 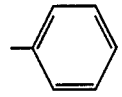 | $OCH_3$ | mp 119~122° C. |
| 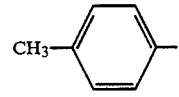 | 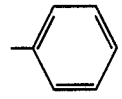 | $CHF_2$ | mp 62~64° C. |
| 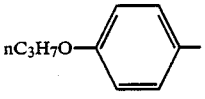 | 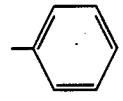 | $CH_3$ | mp 102~104° C. |

TABLE 2-continued
$$A-SO_2\underset{R}{N}-CH_2-\underset{\underset{CH_2}{\overset{O}{\diagdown\diagup}}}{C}-B \qquad (VI)$$
| A | B | R | Physical Constant |
|---|---|---|---|
| 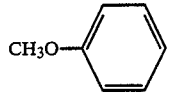 CH₃O— | 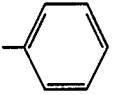 | CH₃ | mp 78~80° C. |
| 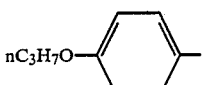 nC₃H₇O— | 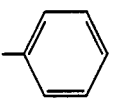 | CH₃ | mp 78.5~81° C. |
| 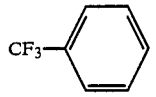 CF₃— | 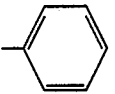 | CH₃ | mp 96~98° C. |
| 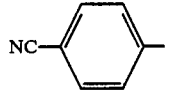 NC— | 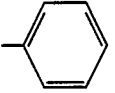 | CH₃ | mp 114~115° C. |
| 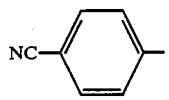 NC— | 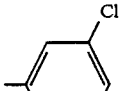 Cl | CH₃ | mp 86~88° C. |
| 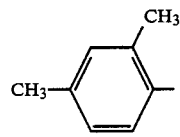 CH₃, CH₃— | 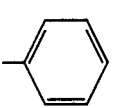 | CH₃ | mp 75~77° C. |
| 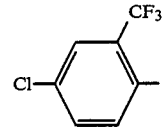 CF₃, Cl— | 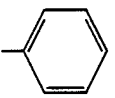 | CH₃ | mp 106~107° C. |
| 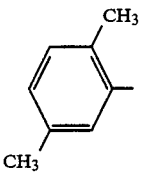 CH₃, CH₃— | 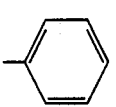 | CH₃ | mp 73~74.5° C. |
| 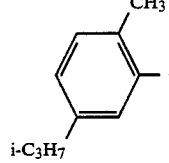 CH₃, i-C₃H₇— | 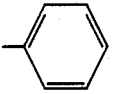 | CH₃ | $n_D^{25}$ 1.5438 |
| 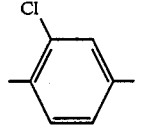 Cl— | 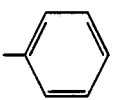 | CH₃ | mp 104~105° C. |

TABLE 2-continued $$A-SO_2N(R)-CH_2-C(B)(-O-CH_2-) \quad (VI)$$

| A | B | R | Physical Constant |
|---|---|---|---|
| 4-Cl-2-CH₃-phenyl | phenyl | CH₃ | mp 109.5~111.5° C. |
| 4-Cl-2-CH₃-phenyl | phenyl | CHF₂ | $n_D^{25.5}$ 1.5449 |
| 4-Cl-2-CH₃-phenyl | 3-Cl-phenyl | CH₃ | mp 78~79° C. |
| 3,4-(CH₃)₂-phenyl | phenyl | CH₃ | mp 108.5~111° C. |
| 4-CN-2-CH₃-phenyl | phenyl | CH₃ | mp 107~109° C. |
| 3,4-(CH₃O)₂-phenyl | 3-Cl-phenyl | CH₃ | mp 116~118° C. |
| 2,3-dihydro-1H-inden-5-yl | phenyl | CH₃ | mp 123~124° C. |
| 5,6,7,8-tetrahydronaphthalen-2-yl | phenyl | CH₃ | mp 118~119° C. |
| 5,6,7,8-tetrahydronaphthalen-2-yl | phenyl | CHF₂ | $n_D^{25.5}$ 1.5502 |
| 2,3-dihydrobenzofuran-5-yl | phenyl | CH₃ | mp 103~104° C. |

TABLE 2-continued $$A-SO_2N(R)-CH_2-\underset{\underset{CH_2}{\diagup\!\!\diagdown\!O}}{C}-B \quad (VI)$$

| A | B | R | Physical Constant |
|---|---|---|---|
| 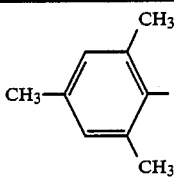 (2,4,5-trimethylphenyl: CH₃ at positions shown) | phenyl | CH₃ | mp 79.5~81° C. |

REFERENCE EXAMPLE 9

Preparation of 3-[N-(4-chlorophenylsulfonyl)-N-methylamino]-2-phenylpropane-1,2-diol A mixture of 1.60 g of 4-chloro-N-methyl-N(2-phenyl-2-propenyl)benzenesulfonamide, 3 ml of dichloromethane, 3.60 g of 88% formic acid, and 0.79 g of 30% hydrogen peroxide was stirred at 40° to 50° C. for 3 hours. After evaporation, 2 ml of triethylamine, 2 ml of water and 4 ml of methanol were added to the residue, and the mixture was stirred at room temperature for 4 hours. After evaporation, the residue was purified by silica gel column chromatography (developing solvent: chloroform-ethyl acetate (10:1)) to obtain 1.09 g of the titled compound.

mp: 122° to 123° C.

IR spectrum (KBr) cm$^{-1}$: 3500, 3425, 2930, 1580, 1470, 1390, 1325, 1155, 1090.

$^1$H—NMR spectrum (CDCl$_3$—TMS)δ: 2.50 (3H, s), 2.61 (1H, dd, 3.19, 3.51 (2H, ABq), 3.57 (1H, s), 3.7 to 4.2 (2H, ABqd), 7.3 to 7.8 (9H, M).

REFERENCE EXAMPLE 10

Preparation of 2-(3-chlorophenyl)-3-[N-(4-cyanophenylsulfonyl)-N-methylamino]propane-1,2-diol A mixture of 5.80 g of N-[2-(3-chlorophenyl)-2-propenyl]-4-cyano-N-methylbenzenesulfonamide and 20 ml of 88% formic acid was stirred at 60° to 70° C. for 6 hours. After evaporation, were added 10 ml of triethylamine, 10 ml of water and 30 ml of methanol, and the mixture was stirred at 40° C. for 4 hours. After evaporation, the residue was purified by silica gel column chromatography (developing solvent: chloroform-ethyl acetate (5:1)) to obtain 4.56 g of the titled compound.

$n_D^{25}$ 1.5746.

IR spectrum (neat) cm$^{-1}$: 3500, 2930, 2235, 1595, 1570.

$^1$H—NMR spectrum (CDCl$_3$—TMS)δ: 2.63-(3H, s), 2.76-(1H, br), 3.22, 3.57-(2H, ABq), 3.65-(1H, s), 3.8 to 4.1-(2H, m), 7.34-(3H, br), 7.54-(1H, br), 7.90-(4H, s).

REFERENCE EXAMPLE 11

Preparation of 3-[N-(2,5-dimethylphenylsulfonyl)-N-methyl-amino]-2-phenylpropane-1,2-diol (a) Preparation of 1-acetoxy-3-[N-(2,5-dimethylphenylsulfonyl)-N-methylamino]-2-phenyl-2-propanol A mixture of 5.30 g of 1,2-epoxy-2-phenyl-3-[N-(2,5-dimethylphenylsulfonyl)-N-methylamino]propane which had been prepared in accordance with Reference Examples 4 to 8, 3.30 g of anhydrous sodium acetate and 50 ml of acetic acid was stirred at 100° to 110° C. for 2 days. After evaporation, the residue was dissolved in 150 ml of benzene, washed subsequently with water, a saturated aqueous sodium bicarbonate and saturated brine, and then dried over anhydrous magnesium sulfate. After evaporation, the residue was purified by silica gel column chromatography (developing solvent: n-hexane-ethyl acetate (5:1)) to obtain 3.60 g of the titled compound.

mp: 84° to 85° C.

IR spectrum (neat) cm$^{-1}$: 3490, 2930, 1740, 1490, 1445, 1375, 1320, 1145.

$^1$H—NMR spectrum (CDCl$_3$—TMS)δ: 2.03-(3H, s), 2.36-(3H, s), 2.53-(3H, s), 2.64-(3H, s), 3.35, 3.82 (2H, ABq), 3.72-(1H, s), 4.47-(2H, s), 7.2 to 7.7-(8H, m).

(b) Preparation of 3-[N-(2,5-dimethylphenylsulfonyl)-N-methylamino]-2-phenylpropane-1,2-diol A mixture of 3.50 g of 1-acetoxy-3-[N-(2,5-dimethylphenylsulfonyl)-N-methylamino]-2-phenyl-2-propanol prepared in the above-described way, 3 ml of triethylamine, 3 ml of water and 6 ml of methanol was stirred at room temperature for 4 hours. After distilling off the solvent, the residue was purified by silica gel column chromatography (developing solvent: benzene-ethyl acetate (4:1)) to obtain 2.80 g of the titled compound.

mp: 114° to 115° C.

IR spectrum (KBr) cm$^{-1}$: 3400, 2915, 1485, 1445, 1340, 1280, 1205.

$^1$H—NMR spectrum (CDCl$_3$—TMS)δ: 2.38-(3H, s), 2.56-(6H, s), 2.63-(1H, t), 3.41, 3.75-(2H, ABq), 3.71 (1H, s), 3.7 to 4.2-(2H, ABqd), 7.3 to 7.7 (8H, m).

REFERENCE EXAMPLE 12

Synthesis of 3-[N-(4-chloro-3-methylbenzenesulfonyl)-N-difluoromethylamino]-1,2-dihydroxy-2-phenylpropane (a) Preparation of 3-[N-(4-chloro-3-methylbenzenesulfonyl)]amino-2-phenylpropane To a mixture of 35 g of 3-amino-2-phenylpropane, 11.0 g of 95% sodium hydroxide and 500 ml of water, 59 g of 4-chloro-3-methylbenezenesulfonyl chloride was added under ice cooling, and the resultant mixture was stirred for 1 hour. The precipitated crystals were collected by suction, washed with water and dried to obtain 79.2 g of the titled compound.

mp: 73° to 74° C.

$^1$H—NMR spectrum (CDCl$_3$—TMS)δ: 2.4-(3H, s), 4.03-(2H, s), 5.2-(1H, s), 5.36-(1H, s), 7.2 to 7.7-(8H, m).

(b) Preparation of 3-[N-(4-chloro-3-methylbenzenesulfonyl)]amino-1,2-dihydroxy-2-phenylpropane To a mixture of 36.3 ml of 30% hydrogen peroxide solution and 350 ml of formic acid, was added 69.0 g of 3-[N-(4-chloro-3-methylbenzenesulfonyl)]amino-2-phenylpropane obtained in the above-described way and the resultant mixture was stirred at 50° to 60° C. for 3 hours. The reaction mixture was concentrated under a reduced pressure. To the residue, were added 50 ml of triethylamine, 50 ml of water and 400 ml of methanol, and the mixture was stirred at 60° to 70° C. for 3 hours. After evaporation, the residue was purified by silica gel column chromatography (developing solvent: chloroform-ethyl acetate (5:1)) to obtain 26.7 g of the titled compound.

mp: 105° to 106° C.

$^1$H—NMR spectrum (CDCl$_3$, DMSO—d$_6$—TMS): 2.4-(3H, s), 3.1 to 3.5-(2H, ABqd), 3.73-(1H, s), 3.6 to 3.8 (2H, m), 4.30-(1H, s), 6.26-(1H, t), 7.2 to 7.8-(8H, m).

(c) Preparation of 3-[N-(4-chloro-3-methylbenzenesulfonyl)-N-difluoromethyl]amino-1,2-dihydroxy-2-phenylpropane A mixture of 24.0 g of 3-[N-(4-chloro-3-methylbenzenesulfonyl)]amino-1,2-dihydroxy-2-phenylpropane prepared in the above-described way, 12.3 g of 2,4-dimethoxybenzaldehyde, 0.25 g of p-tolunenesulfonic acid and 200 ml of toluene was refluxed for 4 hours with azeotropic removal of the resultant water. After cooling, was added 150 ml of toluene, and resultant mixture was washed subsequently with a saturated aqueous sodium bicarbonate, water and saturated brine, and then dried over anhydrous sodium sulfate. To the toluene solution, were added 0.5 g of tetra-n-butylammonium bromide and 20 g of 50% aqueous sodium hydroxide, and chlorodifluoromethane gas was passed into the mixture for 30 minutes with stirring at 80° C. After cooling, the reaction mixture was washed with water and saturated brine. After evaporation, was added 100 ml of 80% acetic acid, then the mixture was stirred at 40° C. for 3 hours. The reaction mixture was diluted with 500 ml of chloroform, washed subsequently with water, a 2N sodium hydroxide, water and saturated brine, and dried over anhydrous magnesium sulfate. After distilling off the solvent, the residue was purified by silica gel column chromatography (developing solvent: chloroform-ethyl acetate (25:1)) to obtain 13.8 g of the intended compound.

mp: 77° to 78° C.

$^1$H—NMR spectrum (CDCl$_3$-TMS)δ: 2.15-(1H, t), 2.46-(3H, s), 3.53, 3.73-(2H, ABqd), 3.85-(2H, s), 3.93 (1H, s), 6.87-(1H, t), 7.3 to 7.7-(8H, m).

The compounds prepared in accordance with Reference Examples 9 to 12 are shown in Table 3.

TABLE 3

$$A-SO_2N(R)-CH_2-C(OH)(CH_2-OH)-B \quad (V)$$

| A | B | R | Physical Constant |
|---|---|---|---|
| phenyl | phenyl | CH$_3$ | mp 131~132° C. |
| 4-F-phenyl | phenyl | CH$_3$ | mp 142~143° C. |
| 4-Cl-phenyl | phenyl | CH$_3$ | mp 122~123° C. |
| 4-Br-phenyl | phenyl | C$_2$H$_5$ | mp 86~87° C. |
| 4-CH$_3$-phenyl | phenyl | CH$_3$ | mp 78~80° C. |
| 4-CH$_3$-phenyl | phenyl | OCH$_3$ | mp 93~94.5° C. |
| 4-CH$_3$-phenyl | 2-Cl-phenyl | CH$_3$ | mp 82~83° C. |
| 4-n-C$_3$H$_7$-phenyl | phenyl | CH$_3$ | n$_D^{25}$ 1.5573 |
| 2-CF$_3$-phenyl | phenyl | CH$_3$ | mp 73~74° C. |
| 4-NC-phenyl | phenyl | CH$_3$ | mp 96~97° C. |

TABLE 3-continued $$A-SO_2N(R)-CH_2-\underset{\underset{CH_2-OH}{|}}{\overset{\overset{OH}{|}}{C}}-B \quad (V)$$

| A | B | R | Physical Constant |
|---|---|---|---|
| 4-NC-C6H4- | 2-Cl-C6H4- | CH3 | $n_D^{25}$ 1.5746 |
| 3-CH3-4-Cl-C6H3- | C6H5- | CH3 | mp 95.5~96.5° C. |
| 3-CH3-4-Cl-C6H3- | C6H5- | CHF2 | mp 77~78° C. |
| 2,4-(CH3)2-C6H3- | C6H5- | CH3 | mp 114~115° C. |
| 5,6,7,8-tetrahydronaphth-2-yl | C6H5- | CH3 | mp 83.5~84.5° C. |
| 2,3-dihydrobenzofuran-5-yl | C6H5- | CH3 | mp 170~172° C. |

Reference Examples 1 to 12 show examples of intermediates for the compound according to the present invention and processes for the synthesis thereof. The present invention are not restricted by these reference examples.

EXAMPLE 1

Preparation of 1-bromo-3-[N-(4-chlorophenylsulfonyl)-N-methylamino]-2-phenyl-2-propanol A mixture of 0.70 g of 4-chloro-N-(2-phenyl-2-propenyl)benzenesulfonamide prepared in accordance with Reference Example 1, 2.2 g of N-bromosuccinimide, 6 ml of tetrahydrofuran and 4 ml of water was stirred at room temperature for 1 hour. To the reaction mixture, was added 10% aqueous sodium thiosulfate and the resultant mixture was extracted with ethyl acetate. The extract was subsequently washed with water and saturated brine and dried over anhydrous magnesium sulfate. After distilling off the solvent, the residue was purified by silica gel column chromatography (developing solvent: benzene-ethyl acetate (20:1)) to obtain 0.65 g of Compound No. 4 in Table 4.

mp: 84° to 85° C.

IR spectrum (KBr) cm$^{-1}$: 3530, 3100, 3070, 1585, 1475, 1335, 1165, 1095, 985.

$^1$H—NMR spectrum (CDCl3—TMS)δ: 2.68-(3H, s), 3.17-(1H, s), 3.14, 3.68-(2H, ABq), 4.03-(2H, s), 7.2 to 7.7-(9H, m).

EXAMPLE 2

Preparation of 1-bromo-3-[N-methyl-N-(4-methylphenylsulfonyl)amino]-2-phenyl-2-propanol and N-(2,3-dibromo-2-phenylpropyl)-N-methyl-p-toluenesulfonamide A mixture of 0.70 g of N-methyl-4-methyl-N-(2-phenyl-2-propenyl)benzenesulfonamide prepared in accordance with Reference Example 2, 2.2 g of N-bromosuccinimide, 6 ml of tetrahydrofuran, 4 ml of water and 1 ml of dimethylsulfoxide was stirred at room temperature for 1 hour. To the reaction mixture, was added 10% aqueous sodium thiosulfate and the resultant mixture was extracted with ethyl acetate. The extract was subsequently washed with water and saturated saline solution and dried over anhydrous magnesium sulfate. After distilling off the solvent, the residue was purified by silica gel column chromatography (developing solvent: chloroform-ethyl acetate (30:1)) to obtain 0.52 g of Compound No. 8 and 0.40 g of Compound No. 12 in Table 4.

(Compound No. 8)

$n_D^{25}$ 1.5727.

IR spectrum (neat) cm$^{31}$: 3500, 3030, 2930, 1595, 1570, 1430, 1340, 1160, 1090.

$^1$H—NMR spectrum (CDCl3—TMS)δ: 2.41-(3H, s), 2.70-(3H, s), 3.11, 3.64-(2H, ABq), 3.32-(1H, s), 4.00 (2H, s), 7.2 to 7.7-(9H, m).

(Compound No. 12)

mp: 83° to 84° C.

IR spectrum (neat) cm$^{-1}$: 3025, 2925, 1595, 1570, 1475, 1430, 1340, 1160.

$^1$H—NMR spectrum (CDCl3—TMS)δ: 2.43-(6H, s), 3.62, 3.98 (2H, ABq), 4.24, 4.53-(2H, ABq), 7.2 to 7.7 (9H, m).

EXAMPLE 3

Preparation of 1-bromo-3-[N-(4-chloro-3-methylphenylsulfonyl)-N-methylamino]-2-phenyl-2-propanol To a mixture of 3.0 g of 4-chloro-N-methyl-3-methyl-N-(2-phenyl-2-propenyl)benzenesulfonamide prepared in accordance with Reference Example 1, 12 ml of tetrahydrofuran, 3 ml of acetic acid and 3 ml of water, was added dropwise a mixture of 1.38 g of sodium bromide, 3 ml of water and 13.4 ml of an aqueous sodium hypochlorite, and the reaction mixture was stirred at room temperature for 2 hours. After dilution with 100 ml of ethyl acetate, the organic layer was subsequently washed with 10% aqueous sodium thiosulfate and saturated brine. The organic layer was dried over anhydrous magnesium sulfate. After distilling off the solvent, the residue was purified by silica gel column chromatography (developing solvent: benzene-ethyl acetate (20:1)) to obtain 1.60 g of Compound No. 32 in Table 4.

mp: 100.5° to 101.5° C.

IR spectrum (KBr) cm$^{-1}$: 3550, 3030, 1445, 1340, 1210, 1160, 1100, 1045, 980.

$^1$H—NMR spectrum (CDCl$_3$—TMS)δ: 2.43-(3H, s), 2.70-(3H, s), 3.17, 3.70-(2H, ABq), 3.20-(1H, s), 4.04 (2H, s), 7.3 to 7.7-(8H, m).

EXAMPLE 4

Preparation of 1-chloro-3-[N-(4-chloro-3-methylphenylsulfonyl)-N-methylamino]-2-phenyl-2-propanol To a mixture of 1.0 g of 4-chloro-N-methyl-3-methyl-N-(2-phenyl-2-propenyl)benzenesulfonamide, 4 ml of tetrahydrofuran, 1 ml of acetic acid and 1 ml of water, was added 4.5 ml of an aqueous sodium hypochlorite solution, and the resultant mixture was stirred at room temperature for 10 hours. After dilution with ethyl acetate, the organic layer was subsequently washed with 10% aqueous sodium thiosulfate and saturated brine, and then dried over anhydrous magnesium sulfate. After distilling off the solvent, the residue was purified by silica gel column chromatography (developing solvent: benzene-ethyl acetate (20:1)) to obtain 0.35 g of Compound No. 31 in Table 4.

mp: 105° to 107° C.

IR spectrum (neat) cm$^{-1}$: 3500, 2925, 1580, 1560, 1490, 1465, 1380, 1335, 1155.

$^1$H—NMR spectrum (CDCl$_3$—TMS)δ: 2.43-(3H, s), 2.68-(3H, s), 3.17, 3.63-(2H, ABq), 3.27-(1H, s), 4.12 (2H, s), 7.3 to 7.7-(8H, m).

EXAMPLE 5

Preparation of 1-methylsulfonyloxy-3-[N-methyl-N-(4-methylphenylsulfonyl)amino]-2-phenyl-2-propanol A mixture of 0.60 g of 3-[N-methyl-N-(4-methylphenylsulfonyl)amino]-2-phenylpropane-1,2-diol prepared in accordance with Reference Example 9, 0.3 g of methanesulfonyl chloride and 3 ml of pyridine was left overnight at 0° to 5° C. The reaction mixture was poured into ice-water and extracted with ethyl acetate. The extract was subsequently washed with 1N hydrochloric acid, water and saturated brine, and dried over anhydrous magnesium sulfate. After distilling off the solvent, the residue was purified by silica gel column chromatography (developing solvent: chloroform-ethyl acetate (15:1)) to obtain 0.46 g of Compound No. 9 in Table 4.

mp: 98° to 99° C.

IR spectrum (KBr) cm$^{-1}$: 3475, 3030, 2940, 1595, 1570, 1490, 1090, 1040.

$^1$H—NMR spectrum (CDCl$_3$—TMS)δ: 2.43-(3H, s), 2.61-(3H, s), 3.03-(3H, s), 3.12-(1H, d), 3.63-(1H, d), 4.01-(1H, s), 4.54-(2H, s), 7.2 to 7.8-(9H, m).

EXAMPLE 6

Preparation of N-(2,3-dibromo-2-phenylpropyl)-4-chloro-3-methyl-N-methylbenzenesulfonamide To a mixture of 1.0 g of 4-chloro-N-methyl-3-methyl-N-(2-phenyl-2-propenyl)benzenesulfonamide and 5 ml of chloroform, was added dropwise 0.50 g of bromine. The reaction mixture was diluted with chloroform and was subsequently washed with water, 10% aqueous sodium thiosulfate and saturated brine and dried over anhydrous magnesium sulfate. After distilling off the solvent, the residue was purified by silica gel column chromatography (developing solvent: benzene-ethyl acetate (20:1)) to obtain 1.12 g of Compound No. 36 in Table 4.

n$_D^{25}$ 1.6046.

IR spectrum (neat) cm$^{-1}$: 3060, 2980, 2925, 1580, 1565, 1490, 1465, 1440, 1380.

$^1$H—NMR spectrum (CDCl$_3$—TMS)δ: 2.37-(3H, s), 2.45-(3H, s), 3.65, 4.05-(2H, ABq), 4.28, 4.58-(2H, ABq), 7.3 to 7.8-(8H, m).

EXAMPLE 7

Preparation of 1-bromo-3-[N-(4-chloro-3-methylbenzenesulfonyl)-N-difluoromethyl]amino-2-phenyl-2-propanol A mixture of 6.7 g of 3[N-(4-chloro-3-methylbenzenesulfonyl)-N-difluoromethyl]amino-2,3-epoxy-2-phenylpropane, 3.04 g of pyridine hydrobromide, 60 ml of chloroform and 6 ml of N,N-dimethylformamide was refluxed for 5 hours. After cooling, the reaction mixture was washed with water and saturated brine and dried over anhydrous magnesium sulfate. After distilling off the solvent, the residue was purified by silica gel column chromatography (developing solvent: n-hexane-ethyl acetate (20:1)) to obtain 3.4 g of Compound No. 33 in Table 4.

mp: 90° to 92° C.

IR spectrum (KBr) cm$^{-1}$: 3520, 1145, 1350, 1205, 1160, 1125, 1100.

$^1$H—NMR spectrum (CDCl$_3$—TMS)δ: 2.45 (3H, s), 3.57 (1H, s), 3.60, 3.78-(2H, ABqd), 3.92-(2H, s), 6.89 (1H, t), 7.3 to 7.7-(8H, m).

The other compounds shown in Table 4 were prepared in the same way as in the respective Example Nos. listed in Table 4. The structure of the compounds obtained were confirmed by the IR spectra and $^1$H-NMR spectra.

TABLE 4

$$A-SO_2N-CH_2-\underset{\underset{CH_2-Z}{|}}{\overset{\overset{W}{|}}{C}}-B$$
$$\phantom{A-SO_2N-}\underset{R}{|}$$

| Compound No. | A | B | R | W | Z | Physical constant | Example No. |
|---|---|---|---|---|---|---|---|
| 1 | ⌬ | ⌬ | CH$_3$ | OH | OSO$_2$CH$_3$ | mp 109~110° C. | 5 |

TABLE 4-continued $$A-SO_2N(R)-CH_2-C(W)(B)-CH_2-Z$$

| Compound No. | A | B | R | W | Z | Physical constant | Example No. |
|---|---|---|---|---|---|---|---|
| 2 | 4-F-C6H4- | C6H5- | CH3 | OH | Br | $n_D^{25}$ 1.5620 | 1 |
| 3 | 4-F-C6H4- | C6H5- | CH3 | OH | OSO2CH3 | mp 100.5~102° C. | 5 |
| 4 | 4-Cl-C6H4- | C6H5- | CH3 | OH | Br | mp 84~85° C. | 1 |
| 5 | 4-Cl-C6H4- | C6H5- | CH3 | OH | OSO2CH3 | mp 104~105° C. | 5 |
| 6 | 4-Br-C6H4- | C6H5- | C2H5 | OH | Br | $n_D^{25}$ 1.6007 | 1 |
| 7 | 4-Br-C6H4- | C6H5- | C2H5 | OH | OSO2CH3 | mp 90~91° C. | 5 |
| 8 | 4-CH3-C6H4- | C6H5- | CH3 | OH | Br | $n_D^{25}$ 1.5727 | 2 |
| 9 | 4-CH3-C6H4- | C6H5- | CH3 | OH | OSO2CH3 | mp 98~99° C. | 5 |
| 10 | 4-CH3-C6H4- | C6H5- | CH3 | OH | OSO2CH3Cl | $n_D^{25}$ 1.5620 | 5 |
| 11 | 4-CH3-C6H4- | C6H5- | CH3 | OH | OSO2-C6H4-4-CH3 | mp 121~123° C. | 5 |
| 12 | 4-CH3-C6H4- | C6H5- | CH3 | Br | Br | mp 83~84° C. | 2 |
| 13 | 4-CH3-C6H4- | C6H5- | OCH3 | OH | Br | $n_D^{25}$ 1.5620 | 2 |

TABLE 4-continued
$$A-SO_2\underset{R}{N}-CH_2-\underset{\underset{CH_2-Z}{|}}{\overset{\overset{W}{|}}{C}}-B$$
| Compound No. | A | B | R | W | Z | Physical constant | Example No. |
|---|---|---|---|---|---|---|---|
| 14 | 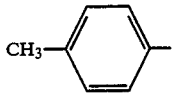 |  | OCH$_3$ | OH | OSO$_2$CH$_3$ | mp 94~95° C. | 5 |
| 15 | 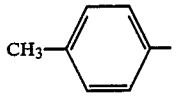 |  | OCH$_3$ | Br | Br | n$_D^{25}$ 1.5806 | 2 |
| 16 | 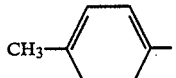 |  | CH$_3$ | OH | Br | n$_D^{25}$ 1.5751 | 2 |
| 17 | 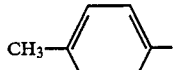 |  | CH$_3$ | OH | OSO$_2$CH$_3$ | mp 98~100° C. | 5 |
| 18 | 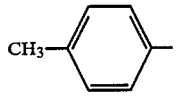 |  | CH$_3$ | Br | Br | mp 84~86° C. | 2 |
| 19 | 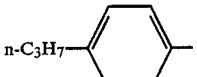 |  | CH$_3$ | OH | Br | n$_D^{25}$ 1.5729 | 1 |
| 20 | 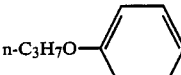 |  | CH$_3$ | OH | Br | n$_D^{25}$ 1.5731 | 1 |
| 21 | 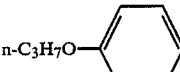 |  | CH$_3$ | OH | OSO$_2$CH$_3$ | mp 104~105° C. | 5 |
| 22 | 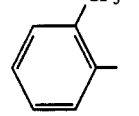 |  | CH$_3$ | OH | Br | n$_D^{25}$ 1.5454 | 1 |
| 23 | 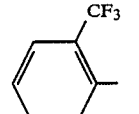 |  | CH$_3$ | OH | OSO$_2$CH$_3$ | mp 101~102° C. | 5 |
| 24 | 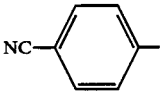 |  | CH$_3$ | OH | Br | mp 105~107° C. | 1 |

TABLE 4-continued $$A-SO_2\underset{R}{N}-CH_2-\underset{\underset{CH_2-Z}{|}}{\overset{\overset{W}{|}}{C}}-B$$

| Compound No. | A | B | R | W | Z | Physical constant | Example No. |
|---|---|---|---|---|---|---|---|
| 25 | 4-NC-C₆H₄- | C₆H₅- | CH₃ | OH | OSO₂CH₃ | mp 166~167° C. | 5 |
| 26 | 4-NC-C₆H₄- | 2-Cl-C₆H₄- | CH₃ | OH | OSO₂CH₃ | mp 72~73° C. | 5 |
| 27 | 4-NC-C₆H₄- | 2-Cl-C₆H₄- | CH₃ | OH | OSO₂C₂H₅ | $n_D^{25}$ 1.5640 | 5 |
| 28 | 4-NC-C₆H₄- | 2-Cl-C₆H₄- | CH₃ | OH | OSO₂C₃H₇-n | $n_D^{25}$ 1.5576 | 5 |
| 29 | 4-NC-C₆H₄- | 2-Cl-C₆H₄- | CH₃ | OH | OSO₂C₄H₉-n | $n_D^{25}$ 1.5529 | 5 |
| 30 | 4-NC-C₆H₄- | 2-Cl-C₆H₄- | CH₃ | OH | OSO₂(CH₂)₃Cl | $n_D^{25}$ 1.5672 | 5 |
| 31 | 4-Cl-3-CH₃-C₆H₃- | C₆H₅- | CH₃ | OH | Cl | mp 105~107° C. | 4 |
| 32 | 4-Cl-3-CH₃-C₆H₃- | C₆H₅- | CH₃ | OH | Br | mp 100.5~101.5° C. | 3 |
| 33 | 4-Cl-3-CH₃-C₆H₃- | C₆H₅- | CHF₂ | OH | Br | mp 90~92° C. | 7 |
| 34 | 4-Cl-3-CH₃-C₆H₃- | C₆H₅- | CH₃ | OH | OSO₂CH₃ | mp 147~148° C. | 5 |

TABLE 4-continued $$A-SO_2N(R)-CH_2-C(W)(CH_2-Z)-B$$

| Compound No. | A | B | R | W | Z | Physical constant | Example No. |
|---|---|---|---|---|---|---|---|
| 35 | 3-CH₃-4-Cl-phenyl | phenyl | CHF₂ | OH | OSO₂CH₃ | mp 120~121.5° C. | 5 |
| 36 | 3-CH₃-4-Cl-phenyl | phenyl | CH₃ | Br | Br | n_D^{25} 1.6046 | 6 |
| 37 | 2,4-(CH₃)₂-phenyl | phenyl | CH₃ | OH | Br | mp 128~128.5° C. | 1 |
| 38 | 2,4-(CH₃)₂-phenyl | phenyl | CH₃ | OH | OSO₂CH₃ | n_D^{25} 1.5567 | 5 |
| 39 | 5,6,7,8-tetrahydronaphthyl | phenyl | CH₃ | OH | Br | mp 72~73° C. | 1 |
| 40 | 5,6,7,8-tetrahydronaphthyl | phenyl | CH₃ | OH | OSO₂CH₃ | mp 130.5~131.5° C. | 5 |
| 41 | 5,6,7,8-tetrahydronaphthyl | phenyl | CHF₂ | OH | OSO₂CH₃ | mp 106.5~108° C. | 5 |
| 42 | 2,3-dihydrobenzofuranyl | phenyl | CH₃ | OH | Br | mp 90~91° C. | 1 |
| 43 | 2,3-dihydrobenzofuranyl | phenyl | CH₃ | OH | OSO₂CH₃ | mp 125~127° C. | 5 |

Examples of formulation processes for preparing a herbicidal composition from the compound according to the present invention will be shown in the following.

FORMULATION EXAMPLE 1

Wettable Powder 40 parts of the compound of the present invention (Compound No. 8 in Table 4), 20 parts of Carplex #80-(trade name:produced by Shionogi & Co., Ltd.), 35 parts of N,N-Kaolin Clay (trade name:Produced by Tsuchiya Kaolin Co., Ltd.) and 5 parts of higher alcohol sulfate purfectant Sorpol 8070-(trade name:produced by Toho Kagaku Co., Ltd.) were uniformly mixed and pulverized to obtain a wettable powder containing 40% of an effective ingredient.

EXAMPLE OF PROCESS 2

Granules 4 parts of the compound of the present invention (Compound No. 24 in Table 4), 42 parts of clay (produced by Nippon Talc Co., Ltd.), 52 parts of bentonite (produced by Hojun Yoko Co., Ltd.) and 2 parts of a succinate surfactant Aerol CT-1-(trade name:produced by Toho Kagaku Co., Ltd.) were mixed and pulverized. The resultant mixture was kneaded with 20 parts of water and extruded from the nozzles of 0.6 mm in diameter of an extrusion pelletizer. The extruded pieces were dried at 60° C. for 2 hours and were then cut to a length of 1 to 2 mm, thereby obtaining granules containing 4% of an active ingredient.

EXAMPLE OF PROCESS 3

Emulsifiable concentrate

An emulsifiable concentrate containing 30% of an active ingredient was prepared by dissolving 30 parts of the compound of the present invention (Compound No. 8 in Table 14) into a mixed solvent of 30 parts of xylene and 25 parts of dimethylformamide, and adding 15 parts of a polyoxyethylene surfactant Sorpol 3005X (trade name:produced by Toho Kagaku Co., Ltd.).

EXAMPLE OF PROCESS 4

Flowable concentrate 30 parts of the compound of the present invention (Compound No. 1 in Table 4) was mixed with and dispersed in a mixture of 8 parts of ethylene glycol, 5 parts of Sorpol AC3032-(trade name: Toho Kagaku Co., Ltd.), 0.1 part of xanthane gum and 56.9 parts of water. The thus obtained mixture in the form of slurry was wet.milled by a Dyno mill (produced by Symmal Enterprise Co., Ltd.) to obtain a stable flowable concentrate containing 30% of an active ingredient.

EXPERIMENT

Pot test under the paddy field condition

A plastic pot having an area of 1/5000 are was charged with the alluvial clay loam of a rice field, and the soil was fertilized and plowed while adding an appropriate amount of water thereto. On the thus prepared soil, the seeds of weeds Echinochloa crus-galli, Rotala indica and Scripus juncoides were sown. The seeds were mixed well with the soil in the layer within 1 cm of the surface and 2.1-leaf stage seedlings of rice plants (variety: Akinishiki, height: 13.5 cm, quality:-good) were planted at a depth of about 1 cm (4 plants per pot). Thereafter, the water was maintained at a depth of 3.5 cm, and the tubers of Cyperus serotinus were planted on the surface of the soil (3 tubers per pot).

On the next day and the seven days after the transplantation, a granule which contained the compound No. 1 obtained in Formulation Example 2, each granule containing each of compounds Nos. 2 to 43, which had been obtained in the same way as in Formulation Example 2 and granules which contained 4-n-propyl-N-(2,3-epoxy-2-phenylpropyl)-α-methylbenzylbenzenesulfonamide (hereinunder referred to as "Reference A") or N-(2,3-epoxypropylene)-N-α-methylbenzylbenzenesulfonamide (hereinunder referred to as "Reference B"), respectively, as the active ingredient, and which had been obtained in the same way as in Formulation Example 2 were treated under the flooded surface. Each granule was used in respectively predetermined amounts so that the doses of active ingredients contained were 10 and 5 g/a, respectively. The leaf stage of the weeds at the time of treating were as follows:

Plot treated on the next day after the transplantation;
No weeds were germinated
Plot treated on the seven days after the transplantation;
Echinochloa crus-galli: 1 to 1.5 l
Rotala indica, Scripus juncoides: 1 l
Cyperus serotinus: 3 to 5 cm After the treatment with the granules, a leaching loss of water was given at a rate of 3 cm/day for 2 days. Twenty eight days after the treatment, the herbicidal effect and phytotoxicity by the herbicide were observed, and the results are shown in Tables 5 and 6.

The rating of the herbicidal effect was calculated by the following equation.

$$\left(1 - \frac{\text{weight of the survival terrestrial weeds in the treated plot}}{\text{weight of the survival terrestrial weeds in the untreated plot}}\right) \times 100 = Y(\%)$$

| Herbicidal index | Y (%) |
| --- | --- |
| 0 | 0 to 4 |
| 1 | 5 to 29 |
| 2 | 30 to 49 |
| 3 | 50 to 69 |
| 4 | 70 to 89 |
| 5 | 90 to 100 |

The phytotoxicity by the herbicide on the rice plant was evaluated on the basis of the following criteria:

| Phytotoxicity index | Degree of phytotoxicity |
| --- | --- |
| 0 | No damage |
| 1 | Slight damage |
| 2 | Small damage |
| 3 | Medium damage |
| 4 | Great damage |
| 5 | Serious damage to death |

TABLE 5

| Compound No. | Dose of active ingredient (g/a) | Phyto-toxicity | Herbicidal effect Echino-chloa crus-galli | Rotala indica | Scripus juncoides | Cyperus serotinus |
|---|---|---|---|---|---|---|
| 1 | 10 | 3 | 5 | 5 | 5 | 5 |
|   | 5  | 2 | 5 | 5 | 5 | 5 |
| 2 | 10 | 1 | 5 | 5 | 5 | 5 |
|   | 5  | 0 | 5 | 5 | 5 | 5 |
| 3 | 10 | 1 | 5 | 5 | 5 | 5 |
|   | 5  | 0 | 5 | 5 | 4 | 4 |
| 4 | 10 | 2 | 5 | 5 | 5 | 5 |
|   | 5  | 0 | 5 | 5 | 4 | 5 |
| 5 | 10 | 0 | 5 | 5 | 5 | 5 |
|   | 5  | 0 | 5 | 5 | 4 | 5 |
| 6 | 10 | 0 | 5 | 5 | 5 | 5 |
|   | 5  | 0 | 5 | 5 | 4 | 4 |
| 7 | 10 | 0 | 5 | 5 | 4 | 5 |
|   | 5  | 0 | 5 | 5 | 4 | 4 |
| 8 | 10 | 0 | 5 | 5 | 5 | 5 |
|   | 5  | 0 | 5 | 5 | 5 | 5 |
| 9 | 10 | 0 | 5 | 5 | 5 | 5 |
|   | 5  | 0 | 5 | 5 | 5 | 5 |
| 10 | 10 | 0 | 5 | 5 | 5 | 5 |
|    | 5  | 0 | 5 | 5 | 5 | 5 |
| 11 | 10 | 0 | 5 | 5 | 4 | 5 |
|    | 5  | 0 | 5 | 5 | 4 | 4 |
| 12 | 10 | 0 | 5 | 5 | 4 | 4 |
|    | 5  | 0 | 5 | 5 | 3 | 4 |
| 13 | 10 | 0 | 5 | 5 | 5 | 5 |
|    | 5  | 0 | 5 | 5 | 4 | 4 |
| 14 | 10 | 0 | 5 | 5 | 5 | 5 |
|    | 5  | 0 | 5 | 5 | 4 | 4 |
| 15 | 10 | 0 | 5 | 5 | 5 | 5 |
|    | 5  | 0 | 4 | 5 | 4 | 5 |
| 16 | 10 | 0 | 5 | 5 | 5 | 5 |
|    | 5  | 0 | 5 | 5 | 4 | 5 |
| 17 | 10 | 0 | 5 | 5 | 5 | 5 |
|    | 5  | 0 | 5 | 5 | 5 | 5 |
| 18 | 10 | 0 | 5 | 5 | 5 | 5 |
|    | 5  | 0 | 5 | 5 | 4 | 5 |
| 19 | 10 | 0 | 5 | 5 | 5 | 5 |
|    | 5  | 0 | 5 | 5 | 4 | 4 |
| 20 | 10 | 0 | 5 | 5 | 5 | 5 |
|    | 5  | 0 | 5 | 5 | 4 | 4 |
| 21 | 10 | 0 | 5 | 5 | 5 | 4 |
|    | 5  | 0 | 5 | 5 | 4 | 4 |
| 22 | 10 | 2 | 5 | 5 | 5 | 5 |
|    | 5  | 0 | 5 | 5 | 5 | 5 |
| 23 | 10 | 1 | 5 | 5 | 5 | 5 |
|    | 5  | 0 | 5 | 5 | 5 | 5 |
| 24 | 10 | 2 | 5 | 5 | 5 | 5 |
|    | 5  | 1 | 5 | 5 | 5 | 5 |
| 25 | 10 | 3 | 5 | 5 | 5 | 5 |
|    | 5  | 1 | 5 | 5 | 5 | 5 |
| 26 | 10 | 3 | 5 | 5 | 5 | 5 |
|    | 5  | 1 | 5 | 5 | 5 | 5 |
| 27 | 10 | 2 | 5 | 5 | 5 | 5 |
|    | 5  | 1 | 5 | 5 | 5 | 5 |
| 28 | 10 | 1 | 5 | 5 | 5 | 5 |
|    | 5  | 0 | 5 | 5 | 5 | 5 |
| 29 | 10 | 1 | 5 | 5 | 5 | 5 |
|    | 5  | 0 | 5 | 5 | 5 | 5 |
| 30 | 10 | 2 | 5 | 5 | 5 | 5 |
|    | 5  | 0 | 5 | 5 | 5 | 5 |
| 31 | 10 | 0 | 5 | 5 | 5 | 5 |
|    | 5  | 0 | 5 | 5 | 4 | 5 |
| 32 | 10 | 0 | 5 | 5 | 5 | 5 |
|    | 5  | 0 | 5 | 5 | 4 | 5 |
| 33 | 10 | 0 | 5 | 5 | 5 | 5 |
|    | 5  | 0 | 5 | 5 | 5 | 5 |
| 34 | 10 | 0 | 5 | 5 | 5 | 5 |
|    | 5  | 0 | 5 | 5 | 4 | 4 |
| 35 | 10 | 0 | 5 | 5 | 5 | 5 |
|    | 5  | 0 | 5 | 5 | 5 | 5 |
| 36 | 10 | 0 | 5 | 5 | 5 | 5 |
|    | 5  | 0 | 5 | 5 | 4 | 4 |
| 37 | 10 | 2 | 5 | 5 | 5 | 5 |
|    | 5  | 1 | 5 | 5 | 5 | 5 |
| 38 | 10 | 3 | 5 | 5 | 5 | 5 |
|    | 5  | 1 | 5 | 5 | 5 | 5 |

TABLE 5-continued

| Compound No. | Dose of active ingredient (g/a) | Next day after transplantation | | | | |
|---|---|---|---|---|---|---|
| | | Phyto-toxicity | Echino-chloa crus-galli | Rotala indica | Scripus juncoides | Cyperus serotinus |
| 39 | 10 | 0 | 5 | 5 | 5 | 5 |
| | 5 | 0 | 5 | 5 | 4 | 5 |
| 40 | 10 | 0 | 5 | 5 | 5 | 5 |
| | 5 | 0 | 5 | 5 | 4 | 5 |
| 41 | 10 | 0 | 5 | 5 | 5 | 5 |
| | 5 | 0 | 5 | 5 | 5 | 5 |
| 42 | 10 | 0 | 5 | 5 | 5 | 5 |
| | 5 | 0 | 5 | 5 | 4 | 5 |
| 43 | 10 | 0 | 5 | 5 | 5 | 5 |
| | 5 | 0 | 5 | 5 | 4 | 5 |
| Reference A | 10 | 0 | 0 | 2 | 0 | 0 |
| | 5 | 0 | 0 | 1 | 0 | 0 |
| Reference B | 10 | 1 | 5 | 5 | 5 | 0 |
| | 5 | 0 | 5 | 5 | 4 | 0 |
| Control | — | 0 | 0 | 0 | 0 | 0 |

TABLE 6

| Compound No. | Dose of active ingredient (g/a) | 7 days after transplantation | | | | |
|---|---|---|---|---|---|---|
| | | Phyto-toxicity | Echino-chloa crus-galli | Rotala indica | Scripus juncoides | Cyperus serotinus |
| 1 | 10 | 1 | 5 | 5 | 5 | 5 |
| | 5 | 0 | 5 | 5 | 4 | 5 |
| 2 | 10 | 0 | 5 | 5 | 5 | 5 |
| | 5 | 0 | 5 | 5 | 4 | 4 |
| 3 | 10 | 0 | 5 | 5 | 5 | 4 |
| | 5 | 0 | 5 | 5 | 4 | 3 |
| 4 | 10 | 0 | 5 | 5 | 5 | 5 |
| | 5 | 0 | 5 | 5 | 3 | 4 |
| 5 | 10 | 0 | 5 | 5 | 5 | 5 |
| | 5 | 0 | 5 | 5 | 3 | 4 |
| 8 | 10 | 0 | 5 | 5 | 5 | 5 |
| | 5 | 0 | 5 | 5 | 4 | 5 |
| 9 | 10 | 0 | 5 | 5 | 5 | 5 |
| | 5 | 0 | 4 | 5 | 4 | 5 |
| 10 | 10 | 0 | 5 | 5 | 5 | 5 |
| | 5 | 0 | 5 | 5 | 4 | 5 |
| 13 | 10 | 0 | 5 | 5 | 4 | 5 |
| | 5 | 0 | 4 | 5 | 3 | 4 |
| 14 | 10 | 0 | 5 | 5 | 4 | 5 |
| | 5 | 0 | 4 | 4 | 3 | 4 |
| 15 | 10 | 0 | 5 | 5 | 5 | 5 |
| | 5 | 0 | 4 | 5 | 4 | 5 |
| 16 | 10 | 0 | 5 | 5 | 5 | 5 |
| | 5 | 0 | 5 | 5 | 4 | 4 |
| 17 | 10 | 0 | 5 | 5 | 5 | 5 |
| | 5 | 0 | 5 | 5 | 4 | 5 |
| 22 | 10 | 1 | 5 | 5 | 5 | 5 |
| | 5 | 0 | 5 | 5 | 5 | 5 |
| 23 | 10 | 0 | 5 | 5 | 5 | 5 |
| | 5 | 0 | 5 | 5 | 4 | 5 |
| 24 | 10 | 1 | 5 | 5 | 5 | 5 |
| | 5 | 0 | 5 | 5 | 5 | 5 |
| 25 | 10 | 1 | 5 | 5 | 5 | 5 |
| | 5 | 0 | 5 | 5 | 5 | 5 |
| 26 | 10 | 1 | 5 | 5 | 5 | 5 |
| | 5 | 0 | 5 | 5 | 5 | 5 |
| 27 | 10 | 1 | 5 | 5 | 5 | 5 |
| | 5 | 0 | 5 | 5 | 5 | 5 |
| 30 | 10 | 0 | 5 | 5 | 5 | 5 |
| | 5 | 0 | 5 | 5 | 4 | 4 |
| 32 | 10 | 0 | 5 | 5 | 5 | 5 |
| | 5 | 0 | 5 | 5 | 4 | 4 |
| 33 | 10 | 0 | 5 | 5 | 5 | 5 |
| | 5 | 0 | 5 | 5 | 5 | 5 |
| 34 | 10 | 0 | 5 | 5 | 4 | 4 |
| | 5 | 0 | 4 | 3 | 3 | 3 |
| 35 | 10 | 0 | 5 | 5 | 5 | 5 |
| | 5 | 0 | 5 | 5 | 5 | 5 |
| 37 | 10 | 1 | 5 | 5 | 5 | 5 |
| | 5 | 0 | 5 | 5 | 5 | 5 |
| 38 | 10 | 1 | 5 | 5 | 5 | 5 |
| | 5 | 0 | 5 | 5 | 5 | 5 |
| 39 | 10 | 0 | 5 | 5 | 4 | 5 |
| | 5 | 0 | 5 | 5 | 4 | 4 |
| 40 | 10 | 0 | 5 | 5 | 4 | 5 |
| | 5 | 0 | 5 | 5 | 4 | 4 |
| 41 | 10 | 0 | 5 | 5 | 5 | 5 |
| | 5 | 0 | 5 | 5 | 4 | 5 |
| 42 | 10 | 0 | 5 | 5 | 5 | 5 |
| | 5 | 0 | 5 | 5 | 4 | 4 |
| Reference A | 10 | 0 | 0 | 1 | 0 | 0 |
| | 5 | 0 | 0 | 1 | 0 | 0 |
| Reference B | 10 | 0 | 2 | 5 | 1 | 0 |
| | 5 | 0 | 0 | 2 | 0 | 0 |
| Control | — | 0 | 0 | 0 | 0 | 0 |

*1 Reference A: described in Japanese Patent Application Laid-Open (KOKAI) No. 58-131977 (1983)

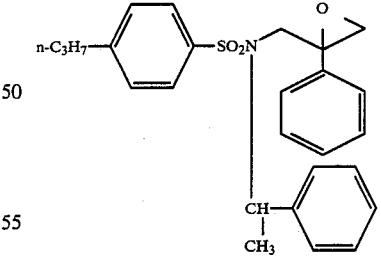

*2 Reference B: described in Japanese Patent Application Laid-Open (KOKAI) No. 58-131977 (1983)

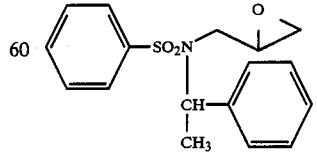

What is claimed is:

1. A sulfonamide compound represented by the following formula (I):

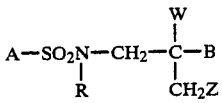 (I)

wherein A represents a group represented by the following formula:

wherein X independently represents a halogen atom, a lower alkyl group, a lower haloalkyl group, a lower alkoxy group, a lower alkylsulfonyl group, a nitro group or a cyano group, and n represents 0 or an integer of 1 to 3, two adjacent Xs being able to represent in combination a group represented by the formula:

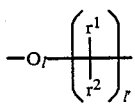

wherein $r^1$ and $r^2$ respectively represents a hydrogen atom or a lower alkyl group, l represents 0 or 1, l' represents an integer of 2 to 4 and the sum of l and l' is 3 or 4; B represents a group represented by the formula:

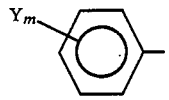

wherein Y independently represents a halogen atom, a lower alkyl group, a lower haloalkyl group or a lower alkoxy group, and m represents 0, 1 or 2; R represents a lower alkyl group, a lower alkoxy group or a lower haloalkyl group; W represents a hydroxyl group or a halogen atom; and Z represents a halogen atom, a lower alkylsulfonyloxy group which may be substituted by halogen atoms, or a phenylsulfonyloxy group which may be substituted by a halogen atom, a lower alkyl group or a lower haloalkoxy group.

2. A herbicidal composition which comprises a herbicidally effective amount of sulfonamide compound represented by the formula (I):

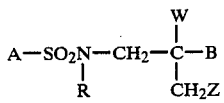 (I)

wherein A represents a group represented by the following formula:

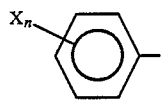

wherein X independently represents a halogen atom, a lower alkyl group, a lower haloalkyl group, a lower alkoxy group, a lower alkylsulfonyl group, a nitro group or a cyano group, and n represents 0 or an integer of 1 to 3, two adjacent Xs being able to represent in combination a group represented by the formula:

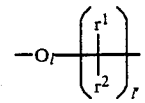

wherein $r^1$ and $r^2$ respectively represents a hydrogen atom or a lower alkyl group, l represents 0 or 1, l' represents an integer of 2 to 4 and the sum of l and l' is 3 to 4; B represents a group represented by the formula:

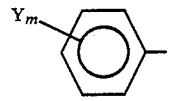

wherein Y independently represents a halogen atom, a lower alkyl group, a lower haloalkyl group or a lower alkoxy group, and m represents 0, 1 or 2; R represents a lower alkyl group, a lower alkoxy group or a lower haloalkyl group; W represents a hydroxy group or a halogen atom; and Z represents a halogen atom, a lower alkylsulfonyloxy group which may be substituted by halogen atoms or a phenylsulfonyloxy group which may be substituted by a halogen atom, a lower alkyl group, a lower haloalkyl group, a lower alkoxy group or a lower haloalkoxy group; and herbicidally acceptable carrier(s) and/or surfactant(s).

3. A method for killing weed which comprises applying a herbicidally effective amount of sulfoamide compound represented by the formula (I):

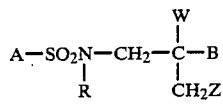 (I)

wherein A represents a group represented by the following formula:

wherein X independently represents a halogen atom, a lower alkyl group, a lower haloalkyl group, a lower alkoxy group, a lower alkylsulfonyl group, a nitro group or a cyano group, and n represents 0 or an integer of 1 to 3, two adjacent Xs being able to represent in combination a group represented by the formula:

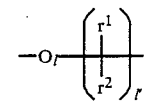

wherein $r^1$ and $r^2$ respectively represents a hydrogen atom or a lower alkyl group, l represents 0 or 1, l' represents an integer or 2 to 4 and the sum of l and l' is 3 or 4; B represents a group represented by the formula:

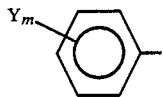

wherein Y independently represents a halogen atom, a lower alkyl group, a lower haloalkyl group or a lower alkoxy group, and m represents 0, 1 or 2; R represents a lower alkyl group, a lower alkoxy group or a lower haloalkyl group; W represents a hydroxyl group or a halogen atom; and Z represents a halogen atom, a lower alkylsulfonyloxy group which may be substituted by halogen atoms or a phenylsulfonyloxy group which may be substituted by a halogen atom, a lower alkyl group, a lower haloalkyl group, a lower alkoxy group or a lower haloalkoxy group, on the soil of flooded field or farmland.

4. The sulfonamide according to claim 1, 1-bromo-3-[N-(4-chloro-3-methylbenzenesulfonyl)-N-difluoromethyl]amino-2-phenyl-2-propanol.

5. The herbicidal composition according to claim 2, wherein the sulfonamide compound is 1-bromo-3-[N-(4-chloro-3-methylbenzenesulfonyl)-N-difluoromethyl]amino-2-phenyl-2-propanol.

6. The method according to claim 3, wherein the sulfonamide compound is 1-bromo-3-[N-(-4-chloro-3-methylbenzenesulfonyl)-N-difluoromethyl]amino-2-phenyl-2-propanol.

* * * * *